United States Patent
Vismara et al.

(10) Patent No.: US 12,290,440 B2
(45) Date of Patent: May 6, 2025

(54) DEVICE AND ASSEMBLY TO REPAIR A HEART VALVE

(71) Applicant: Approxima Srl, Seregno (IT)

(72) Inventors: Riccardo Vismara, Milan (IT); Gianfranco Beniamino Fiore, Milan (IT); Michal Jaworek, Seregno (IT); Edoardo Maroncelli, Seregno (IT); Federico Lucherini, Milan (IT); Eleonora Salurso, Milan (IT); Gianmarco Provaroni, Milan (IT); Guido Gelpi, Milan (IT); Claudia Romagnoni, Milan (IT); Monica Contino, Milan (IT)

(73) Assignee: Approxima Srl, Seregno (IT)

( * ) Notice: Subject to any disclaimer, the term of this patent is extended or adjusted under 35 U.S.C. 154(b) by 0 days.

(21) Appl. No.: 18/365,907

(22) Filed: Aug. 4, 2023

(65) Prior Publication Data

US 2023/0380975 A1  Nov. 30, 2023

Related U.S. Application Data

(63) Continuation of application No. 17/992,834, filed on Nov. 22, 2022, now Pat. No. 11,766,331, which is a
(Continued)

(30) Foreign Application Priority Data

May 27, 2020 (IT) .................. 102020000012562

(51) Int. Cl.
*A61F 2/24* (2006.01)
(52) U.S. Cl.
CPC .... *A61F 2/2487* (2013.01); *A61F 2220/0075* (2013.01); *A61F 2250/0007* (2013.01)

(58) Field of Classification Search
None
See application file for complete search history.

(56) References Cited

U.S. PATENT DOCUMENTS

| | | | |
|---|---|---|---|
| 6,537,198 | B1 | 3/2003 | Vidlund et al. |
| 7,431,692 | B2 | 10/2008 | Zollinger |

(Continued)

FOREIGN PATENT DOCUMENTS

| | | |
|---|---|---|
| CA | 2837206 A1 | 12/2012 |
| CA | 2837206 C | 12/2012 |

(Continued)

OTHER PUBLICATIONS

International Search Report and Written Opinion issued in PCT/IB2021/054150, mailed Sep. 2, 2021.

*Primary Examiner* — Kennedy Schaetzle
(74) *Attorney, Agent, or Firm* — Nelson Mullins Riley & Scarborough LLP

(57) ABSTRACT

An assembly for reshaping a cardiac ventricle in a patient comprising an implantable device for reshaping a ventricle comprising a tether, a non-implantable tool which is detachably connectable to said implantable device and has a proximal portion and a distal portion opposite to said proximal portion; the implantable device further comprises an active anchor adapted to be detachably connected to the distal portion of the tool; the active anchor comprises an abutment portion adapted to abut against a structure of the ventricle; the active anchor of the implantable device comprises an adjustment device adapted to adjust the tensional state of the tether; the distal portion of the tool comprises an adjustment key adapted to cooperate with the adjustment device of the active anchor; the proximal portion of the tool comprises a maneuvering interface which is operatively connectable to said adjustment key for adjusting the ten- (Continued)

sional state of the tether by acting on the maneuvering interface of the proximal portion of the tool.

18 Claims, 14 Drawing Sheets

Related U.S. Application Data continuation of application No. PCT/IB2021/054150, filed on May 14, 2021.

(56) References Cited

U.S. PATENT DOCUMENTS

| | | | |
|---|---|---|---|
| 8,147,542 B2 | 4/2012 | Maisano et al. | |
| 9,597,184 B2 | 3/2017 | Machold et al. | |
| 11,116,497 B2 | 9/2021 | Maisano et al. | |
| 11,766,331 B2 * | 9/2023 | Vismara | A61F 2/2487 600/16 |
| 2003/0078465 A1 | 4/2003 | Pai et al. | |
| 2005/0075723 A1 | 4/2005 | Schroeder | |
| 2005/0197692 A1 | 9/2005 | Pai et al. | |
| 2005/0222488 A1 | 10/2005 | Chang et al. | |
| 2006/0015003 A1 | 1/2006 | Moaddes et al. | |
| 2006/0149123 A1 | 7/2006 | Vidlund et al. | |
| 2007/0073370 A1 | 3/2007 | Zielinski et al. | |
| 2007/0112425 A1 | 5/2007 | Schaller | |
| 2007/0203391 A1 | 8/2007 | Bloom et al. | |
| 2007/0265658 A1 * | 11/2007 | Nelson | A61B 17/0469 606/213 |
| 2008/0086164 A1 | 4/2008 | Rowe | |
| 2008/0195126 A1 | 8/2008 | Solem | |
| 2010/0023117 A1 | 1/2010 | Yoganathan et al. | |
| 2010/0185278 A1 | 7/2010 | Schankereli | |
| 2011/0029071 A1 | 2/2011 | Zlotnick et al. | |
| 2011/0106245 A1 * | 5/2011 | Miller | A61F 2/2442 623/2.11 |
| 2011/0178362 A1 | 7/2011 | Evans et al. | |
| 2012/0191169 A1 | 7/2012 | Rothstein et al. | |
| 2013/0030522 A1 | 1/2013 | Rowe et al. | |
| 2014/0379006 A1 | 12/2014 | Sutherland et al. | |
| 2016/0038130 A1 | 2/2016 | Schaller et al. | |
| 2016/0174964 A1 | 6/2016 | Tobis | |
| 2016/0262741 A1 | 9/2016 | Gilmore et al. | |
| 2017/0086975 A1 | 3/2017 | Gilmore et al. | |
| 2017/0340329 A1 | 11/2017 | Groothuis et al. | |
| 2018/0103947 A1 | 4/2018 | Nobles et al. | |
| 2018/0344311 A1 | 12/2018 | Gilmore et al. | |
| 2019/0133575 A1 | 5/2019 | Maisano et al. | |
| 2019/0167428 A1 | 6/2019 | Tobis | |
| 2019/0274833 A1 | 9/2019 | Van Bladel et al. | |
| 2019/0343626 A1 | 11/2019 | Smirnov et al. | |
| 2019/0343633 A1 | 11/2019 | Garvin et al. | |
| 2019/0343634 A1 | 11/2019 | Garvin et al. | |
| 2019/0350709 A1 | 11/2019 | Maisano et al. | |
| 2019/0365539 A1 | 12/2019 | Rabito et al. | |
| 2019/0380699 A1 | 12/2019 | Bak-Boychuk et al. | |
| 2020/0113685 A1 | 4/2020 | Miller et al. | |
| 2022/0054270 A1 | 2/2022 | Manash | |

FOREIGN PATENT DOCUMENTS

| | | |
|---|---|---|
| CN | 109044565 A | 12/2018 |
| CN | 111772874 A | 10/2020 |
| CN | 109044565 B | 3/2021 |
| CN | 214549745 U | 11/2021 |
| CN | 214804938 U | 11/2021 |
| DE | 102006028964 A1 | 12/2007 |
| EP | 1039851 A1 | 10/2000 |
| EP | 1367962 A2 | 12/2003 |
| EP | 1039851 B1 | 7/2005 |
| EP | 1628599 A2 | 3/2006 |
| EP | 1788983 A2 | 5/2007 |
| EP | 1959866 A1 | 8/2008 |
| EP | 1986735 A2 | 11/2008 |
| EP | 2081519 A2 | 7/2009 |
| EP | 2525741 A1 | 11/2012 |
| EP | 2081519 B1 | 4/2014 |
| EP | 2750631 A1 | 7/2014 |
| EP | 2814427 A1 | 12/2014 |
| EP | 2863844 A1 | 4/2015 |
| EP | 2961351 A1 | 1/2016 |
| EP | 2999435 A1 | 3/2016 |
| EP | 3013250 A1 | 5/2016 |
| EP | 3060175 A1 | 8/2016 |
| EP | 3120611 A3 | 1/2017 |
| EP | 3120811 A2 | 1/2017 |
| EP | 3242629 A1 | 11/2017 |
| EP | 3270794 A1 | 1/2018 |
| EP | 3337428 A1 | 6/2018 |
| EP | 3360515 A1 | 8/2018 |
| EP | 3386440 A1 | 10/2018 |
| EP | 3558169 A1 | 10/2018 |
| EP | 2961351 B1 | 11/2018 |
| EP | 3624705 A1 | 11/2018 |
| EP | 2814427 B1 | 12/2018 |
| EP | 3242629 B1 | 12/2018 |
| EP | 2575685 B1 | 2/2019 |
| EP | 1959866 B1 | 3/2019 |
| EP | 3468506 A1 | 4/2019 |
| EP | 3538028 A1 | 9/2019 |
| EP | 3579761 A2 | 12/2019 |
| EP | 3595587 A1 | 1/2020 |
| EP | 3600143 A1 | 2/2020 |
| EP | 3630014 A1 | 4/2020 |
| EP | 3682852 A1 | 7/2020 |
| EP | 3689258 A1 | 8/2020 |
| EP | 3697346 A1 | 8/2020 |
| EP | 3713518 A1 | 9/2020 |
| EP | 3538028 B1 | 12/2020 |
| EP | 3843664 A1 | 7/2021 |
| EP | 3624705 B1 | 12/2021 |
| EP | 2400922 A1 | 1/2022 |
| EP | 2400922 B1 | 1/2022 |
| EP | 3558169 B1 | 1/2022 |
| EP | 3697346 B1 | 1/2022 |
| EP | 2750631 B1 | 11/2022 |
| EP | 2999435 B1 | 12/2022 |
| WO | 1999030647 A | 6/1999 |
| WO | 2001070116 A1 | 9/2001 |
| WO | 2002030292 A1 | 4/2002 |
| WO | 2009026145 A1 | 2/2009 |
| WO | 2009046343 A1 | 4/2009 |
| WO | 2009081396 A2 | 7/2009 |
| WO | 2009081396 A3 | 7/2009 |
| WO | 2011154942 A2 | 12/2011 |
| WO | 2013049766 A1 | 4/2013 |
| WO | 2013096757 A1 | 6/2013 |
| WO | 2013123388 A1 | 8/2013 |
| WO | 2014141239 A1 | 9/2014 |
| WO | 2014164028 A1 | 10/2014 |
| WO | 2015063580 A2 | 5/2015 |
| WO | 2015063580 A3 | 5/2015 |
| WO | 2015109243 A1 | 7/2015 |
| WO | 2015112971 A1 | 7/2015 |
| WO | 2015151627 A1 | 10/2015 |
| WO | 2015193728 A2 | 12/2015 |
| WO | 2015193728 A3 | 12/2015 |
| WO | 2015193728 A8 | 12/2015 |
| WO | 2016110735 A1 | 7/2016 |
| WO | 2016154498 A1 | 9/2016 |
| WO | 2017087688 A1 | 5/2017 |
| WO | 2017103843 A1 | 6/2017 |
| WO | 2017205358 A1 | 11/2017 |
| WO | 2018145249 A1 | 8/2018 |
| WO | 2018148324 A1 | 8/2018 |
| WO | 2018148364 A2 | 8/2018 |
| WO | 2018148364 A3 | 8/2018 |
| WO | 2018160456 A1 | 9/2018 |
| WO | 20181699878 A1 | 9/2018 |
| WO | 2018183632 A1 | 10/2018 |
| WO | 2018204518 A1 | 11/2018 |
| WO | 2019006152 A1 | 1/2019 |
| WO | 2019173385 A1 | 9/2019 |

(56) References Cited

FOREIGN PATENT DOCUMENTS

| | | |
|---|---|---|
| WO | 2019217638 A1 | 11/2019 |
| WO | 2019217638 A9 | 11/2019 |
| WO | 20190343633 A1 | 11/2019 |
| WO | 2019231744 A1 | 12/2019 |
| WO | 2020032925 A1 | 2/2020 |
| WO | 2020096861 A1 | 5/2020 |
| WO | 2020150497 A1 | 7/2020 |
| WO | 2020167456 A1 | 8/2020 |
| WO | 2020176201 A1 | 9/2020 |
| WO | 2020227556 A1 | 11/2020 |
| WO | 2020231237 A2 | 11/2020 |
| WO | 2020231237 A3 | 11/2020 |
| WO | 2020236417 A1 | 11/2020 |
| WO | 2021024183 A1 | 2/2021 |
| WO | 2021150913 A1 | 7/2021 |
| WO | 2021240289 A1 | 12/2021 |

* cited by examiner

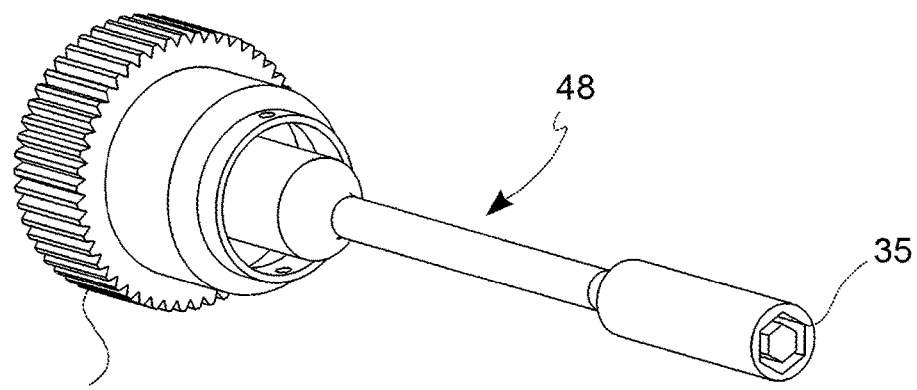
FIG. 18
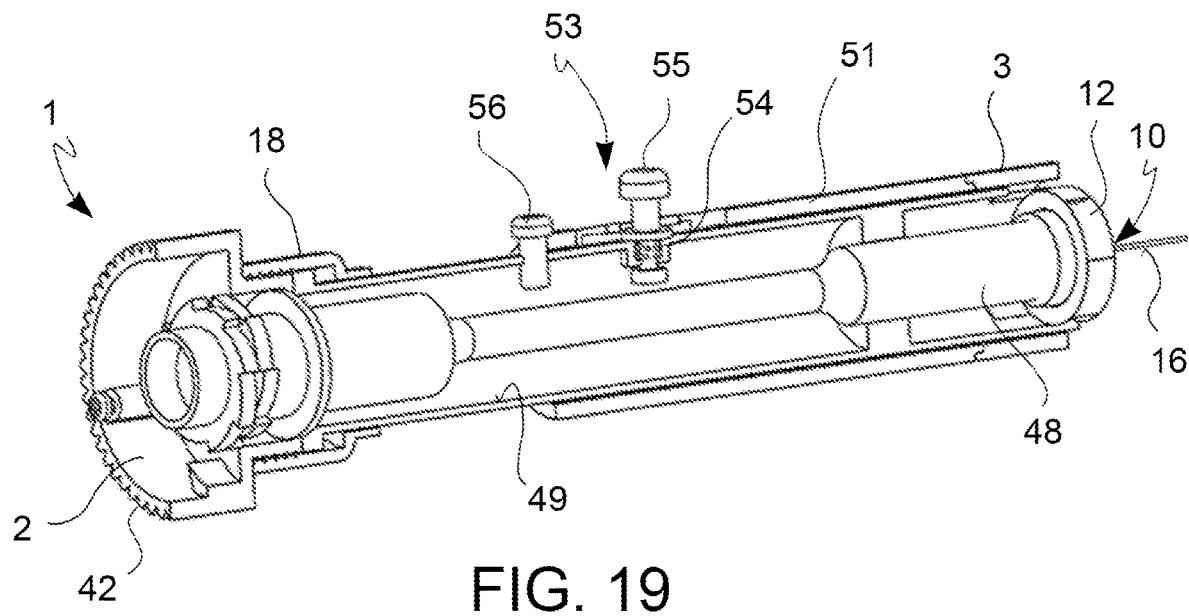
FIG. 19
FIG. 20A

DEVICE AND ASSEMBLY TO REPAIR A HEART VALVE

CROSS REFERENCE TO RELATED APPLICATIONS

The present application is a continuation of U.S. patent application Ser. No. 17/992,834, filed Nov. 22, 2022, which is a continuation of PCT Patent Application No. PCT/IB2021/054150, internationally filed May 14, 2021, which claims priority to Italian Patent Application No. 102020000012562, filed May 27, 2020. All prior applications are incorporated herein by reference in their entirety.

FIELD OF THE INVENTION

The present invention relates to the technical domain of heart valve repair systems.

In particular, the present invention relates to valve repair according to an approach which includes the relative bringing together of native ventricle structures.

The present invention relates to an assembly to repair a heart valve.

BACKGROUND

A native atrioventricular heart valve can become damaged and unable to close effectively. A typical type of damage is related to the structural alteration of the ventricle which is dilated; the muscular-fibrous ring forming the passage opening can also be dilated. These alterations cause the inability of the valve leaflets to arrange themselves in the coaptation position and necessarily cause a highly undesirable regurgitation flow from the ventricle towards the atrium which in turn severely limits the effectiveness of the heart pump.

Typically, for the repair of an atrioventricular valve, for example the mitral valve, a hoop ring is implanted to reinforce the annulus so as to return the annulus to the original shape thereof, thus allowing the free margin of the leaflets to be brought closer together with the valve closed.

Devices which are implantable via trans-catheter have also been proposed in the form of a clip for capturing and bringing the free edge of the valve leaflets closer together, resulting in the formation of a double orifice valve, following the example of the Alfieri suture.

A further known approach includes the implantation of devices for bringing the walls of the heart chambers (atria and ventricles) closer together or bringing the papillary muscles forming the anchoring structures of the tendon to the inner side of the ventricle closer together.

For example, US-2017-0086975 shows a solution which includes fixing a tether between two atrial walls near the valve to be repaired. A similar solution is also shown by US-2005-222488. US-2007-203391 shows a tether for bringing the ventricular walls closer together. For example, US-2019-380699 shows a device which is implantable in the left ventricle via trans-catheter having a pair of rigid plates which are fixed on the outer side of the papillary muscles, i.e., the side facing the ventricular wall, and a thread-like structure, such as a suture filament, extending therebetween.

All the solutions of the types described above are intrinsically unsuitable for allowing a precise adjustment of the degree of bringing the ventricular walls together, particularly after implantation, and could involve the replacement of the implantable device.

US-2019-0365539 includes the implantation inside the right ventricle of an accordion element coupled to two opposing inner ventricular walls, the device being preloaded with a spring so as to influence the walls to which it is coupled, bringing them together. Although advantageous from some points of view, this solution risks excessively stressing the ventricular walls in the first moments after implantation due to the elastic action exerted by the spring, effectively squeezing the ventricular chamber. Furthermore, the coupling of the device to the inner wall of the heart can fail very early under the elastic action of the spring.

The need is therefore felt to provide a solution to repair an atrioventricular valve which is of improved efficacy in both the short and long term.

SUMMARY

In Example 1, an assembly for reshaping a cardiac ventricle in a patient comprises: an implantable device for reshaping a cardiac ventricle comprising a tether; a non-implantable tool which is detachably connectable to said implantable device and has a proximal portion and a distal portion opposite to said proximal portion; wherein: the implantable device further comprises an active anchor adapted to be detachably connected to the distal portion of the tool, and a second anchor opposite to said active anchor with respect to said tether. The active anchor comprises an abutment portion adapted to abut against a structure of the cardiac ventricle; the active anchor of the implantable device comprises an adjustment device adapted to adjust the tensional state of the tether, the adjustment of the tensional state of the tether is preferably obtained by varying the useful length of the tether, i.e., the working length of the tether between the two anchors; the distal portion of the tool comprises an adjustment key adapted to cooperate with the adjustment device of the active anchor; the proximal portion of the tool comprises a maneuvering interface which is operatively connectable to said adjustment key for adjusting the tensional state of the tether by acting on the maneuvering interface of the proximal portion of the tool.

Example 2 is the assembly according to Example 1, wherein the tool also acts as a delivery tool of the active anchor of the implantable device.

Example 3 is the assembly according to Examples 1 or 2, wherein the tool is a trans-thoracic tool.

Example 4 is the assembly according to any one of the preceding examples, wherein a proximal section of the tether comprises an enlarged part, for example a knot, to stop the adjustment of the tensional state of the tether.

Example 5 is the assembly according to any one of the preceding examples, wherein the adjustment device of the active anchor of the implantable device comprises two portions rotatably associated with each other.

Example 6 is the assembly according to Example 5, wherein the tool further comprises a shaft fitted onto said adjustment key, so that the adjustment key and the shaft are rotatably associated with each other, and wherein the adjustment key is integrally connectable to a first portion of the adjustment device of the active anchor, and wherein the shaft is integrally connectable to a second portion of the adjustment device of the active anchor.

Example 7 is the assembly according to Examples 5 or 6, wherein a portion of said two portions of the adjustment device is integrally connectable to the tether.

Example 8 is the assembly according to Examples 5, 6 or 7, wherein a portion of said two portions comprises a winding shaft for winding the tether.

Example 9 is the assembly according to any one of Examples 5 to 8, wherein said two portions are rotatably associated with each other by means of a threaded coupling.

Example 10 is the assembly according to any one of Examples 1 to 4, wherein the adjustment device of the active anchor of the implantable device comprises an expandable element, for example an inflatable balloon.

Example 11 is the assembly according to any one of the preceding claims, wherein the active anchor of the implantable device comprises an anchor back opposite to said abutment portion, wherein the distal portion of the tool is detachably connectable to said anchor back; and/or wherein the anchor back is adapted to remain outside the ventricle.

Example 12 is the assembly according to any one of the preceding claims, wherein the tool comprises an outer case slidingly associated with said shaft so that the distal portion of the tool can protrude at various distances distally from the outer case.

Example 13 is the assembly according to any one of the preceding examples, wherein the tool comprises a tether guiding device adapted to guide a proximal section of the tether to allow the pre-assembly of the active anchor of the implantable device on the tool.

Example 14 is the assembly according to any one of the preceding examples, further comprising a cardiac catheter for the adjustment of the tether, wherein the cardiac catheter preferably comprises at the distal end thereof an elastic clip so as to deliver it inside the cardiac ventricle in order to adjust the tensional state of the tether.

Example 15 is the assembly according to any one of the preceding examples, comprising a vascular catheter for the delivery of at least one portion of the implantable device.

DRAWINGS

Further features and advantages of the invention will become apparent from the description provided below of preferred exemplary embodiments thereof, given by way of non-limiting example, with reference to the accompanying drawings, in which:

FIG. 1 diagrammatically shows an implantable device when implanted in a patient, according to an embodiment;

FIG. 2 diagrammatically shows an assembly comprising a tool and an implantable device when implanted in a patient, according to an embodiment;

Figure 1:
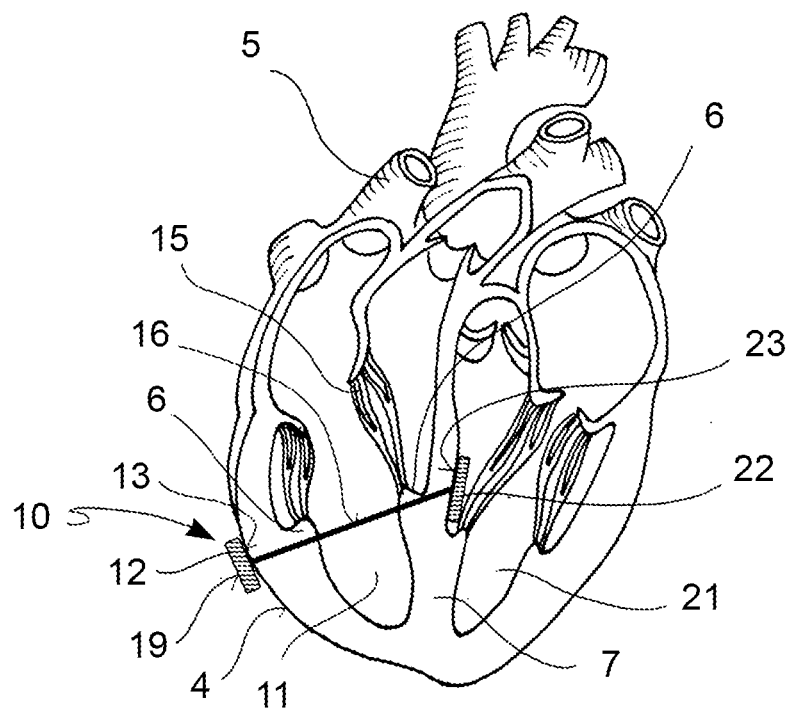
Figure 2:
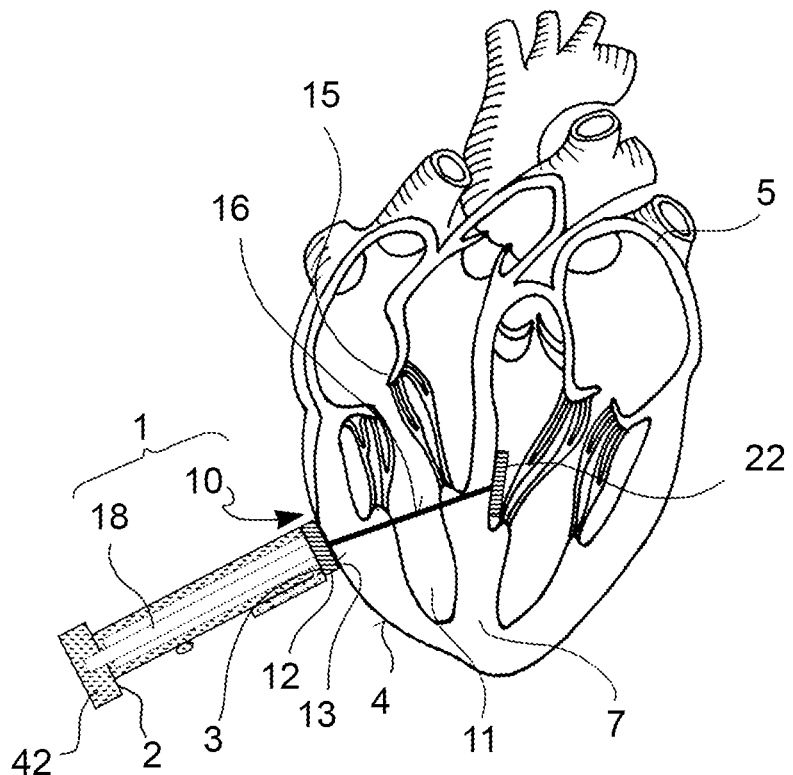
Figure 3:
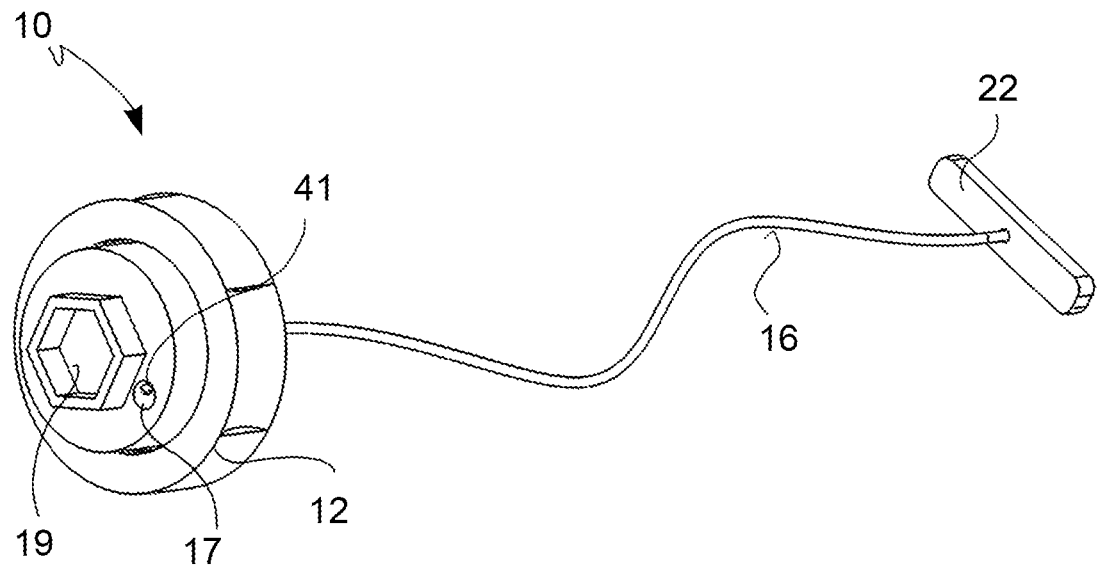
FIG. 3 shows an axonometric view of an implantable device, according to an embodiment.
Figure 4:
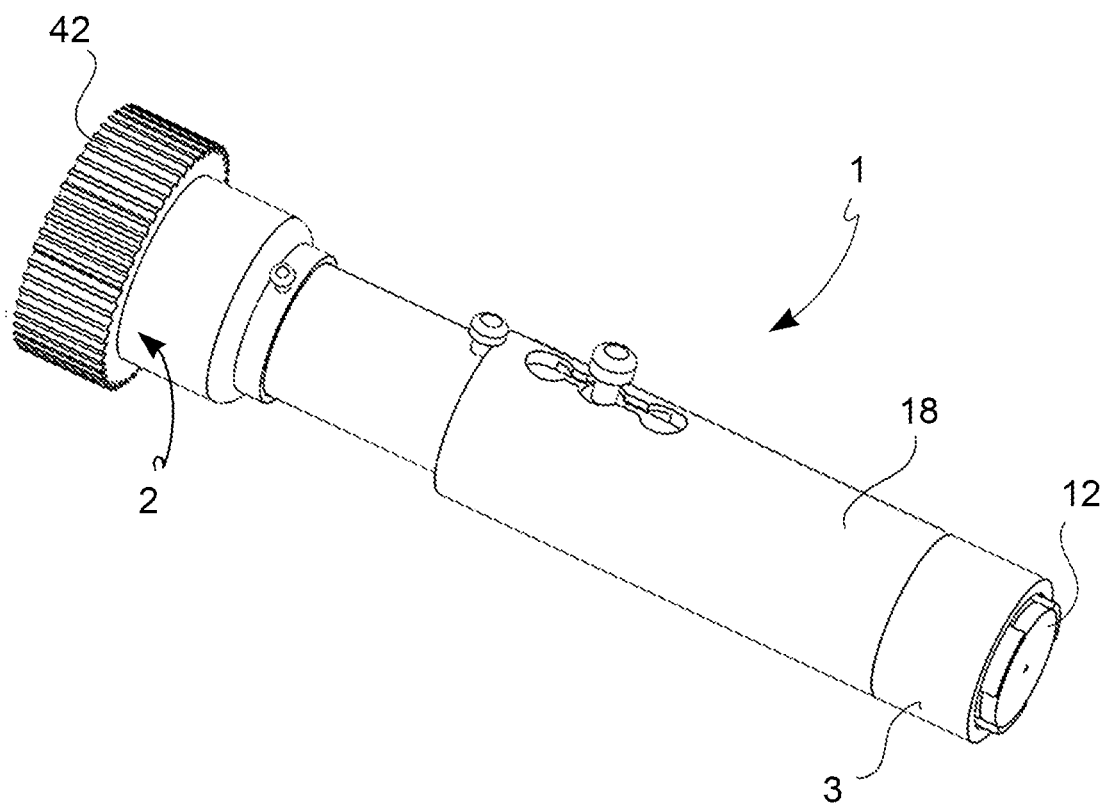
FIG. 4 shows an axonometric view of an assembly comprising a tool and an implantable device, according to an embodiment.
Figure 5A:
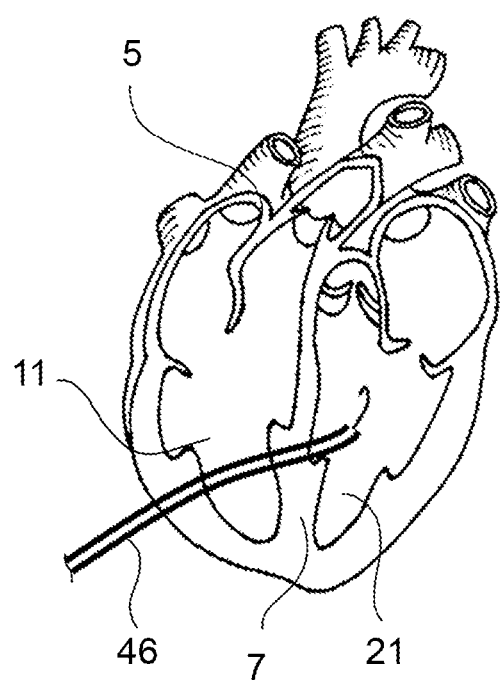
Figure 5B:
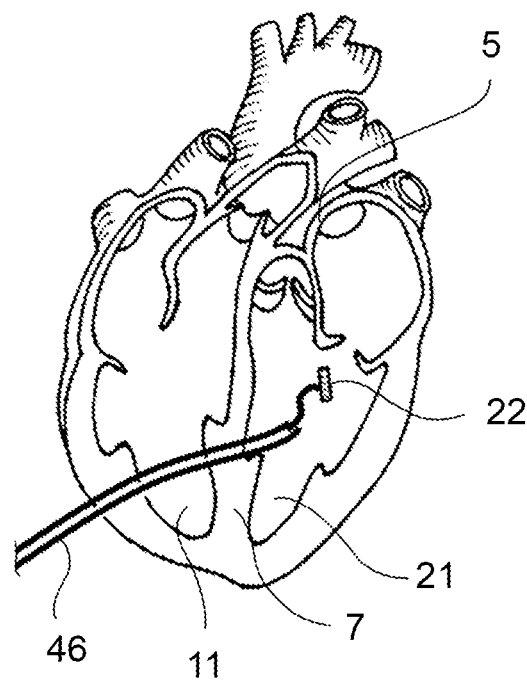
Figure 6:
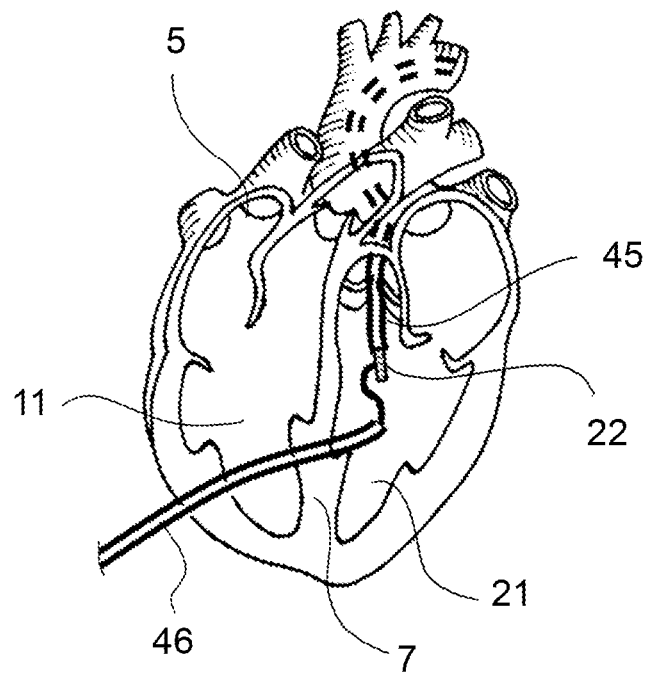
Figure 7A:
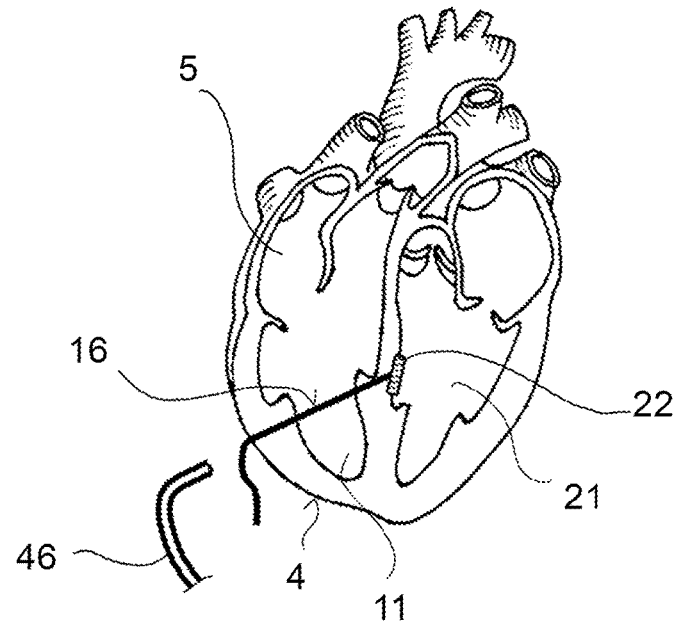
Figure 7B:
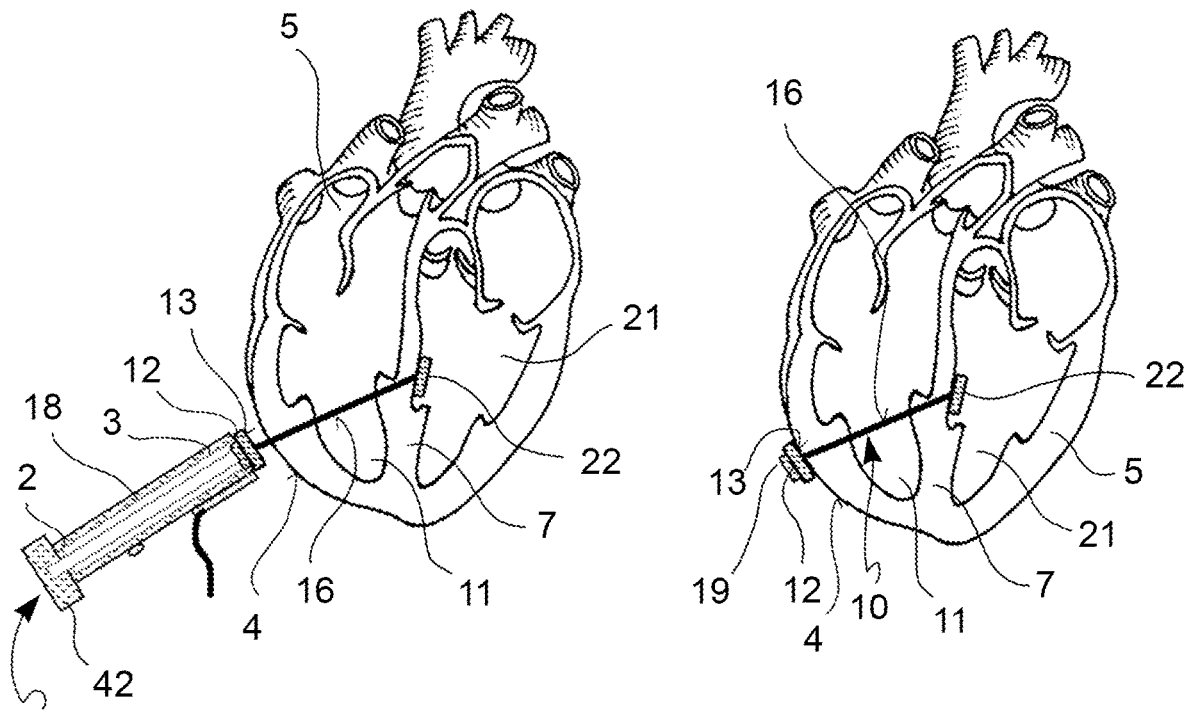
Figure 7C:
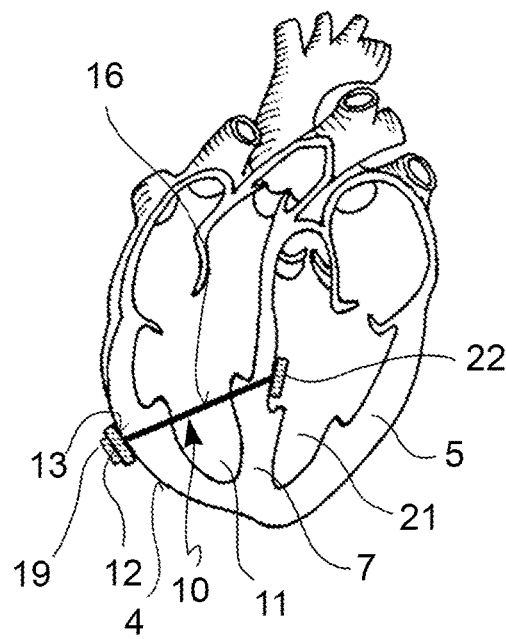
Figure 8:
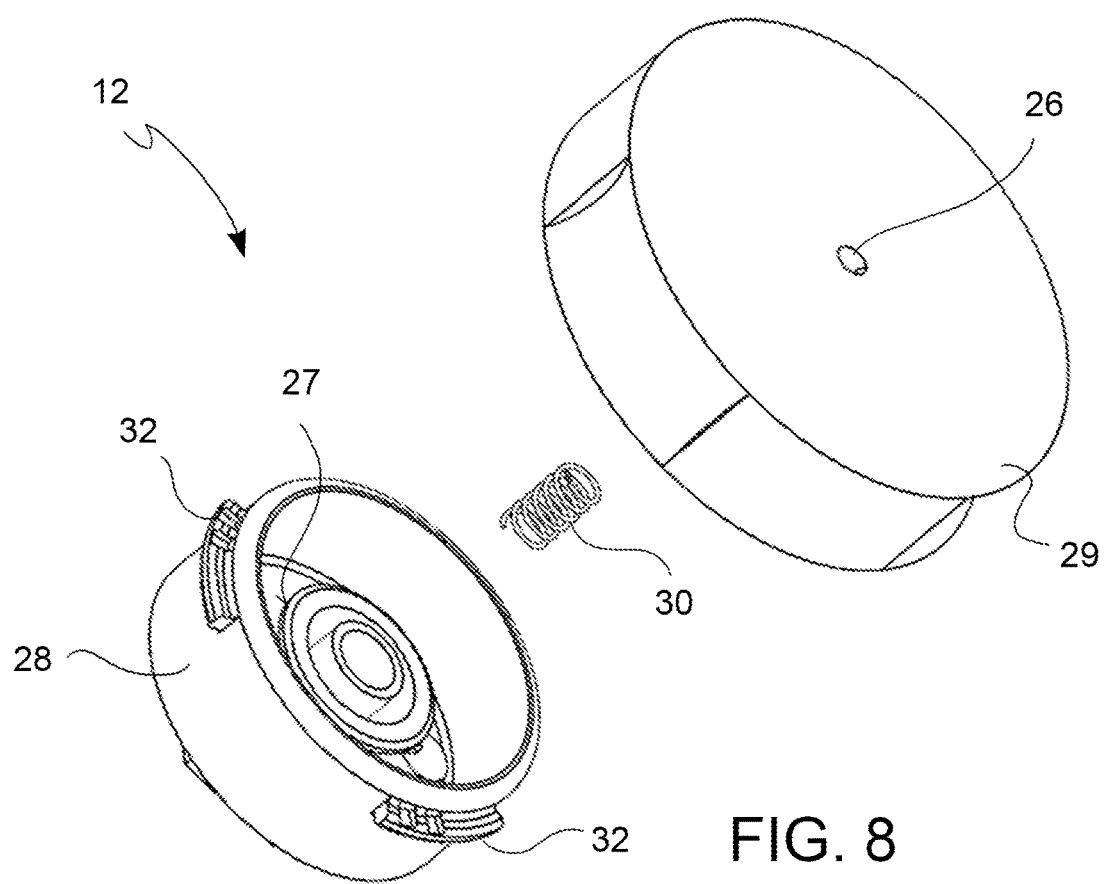
Figure 9A:
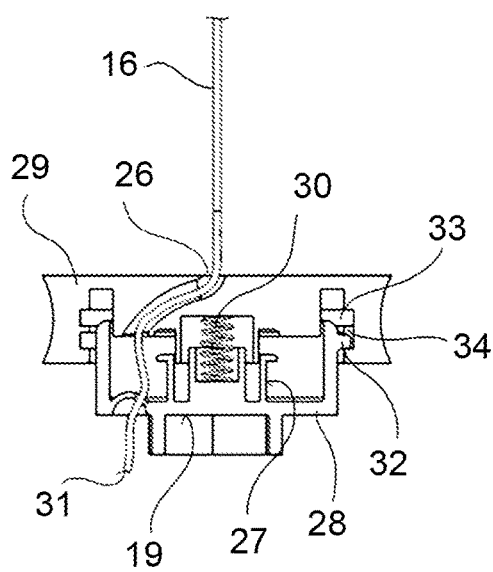
Figure 9B:
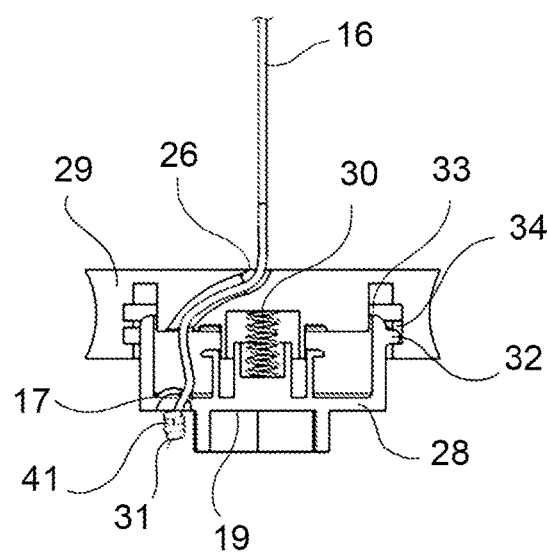
Figure 9C:
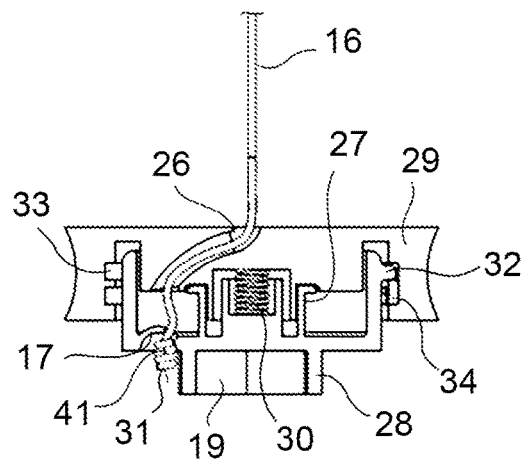
Figure 9D:
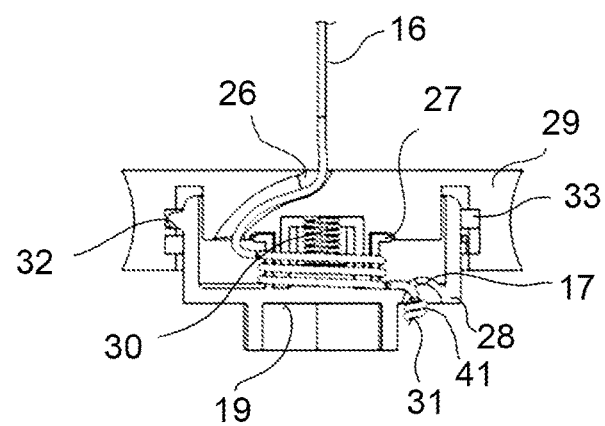
Figure 9E:
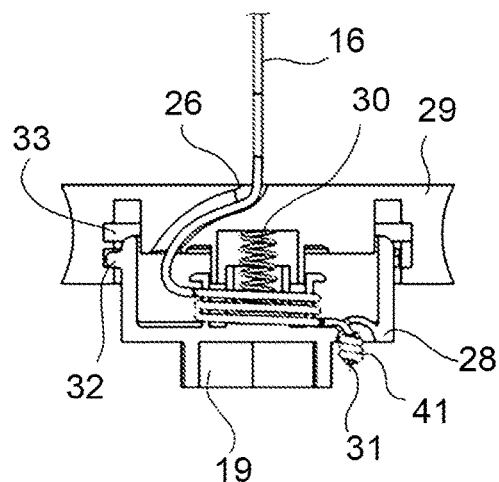
Figure 9F:
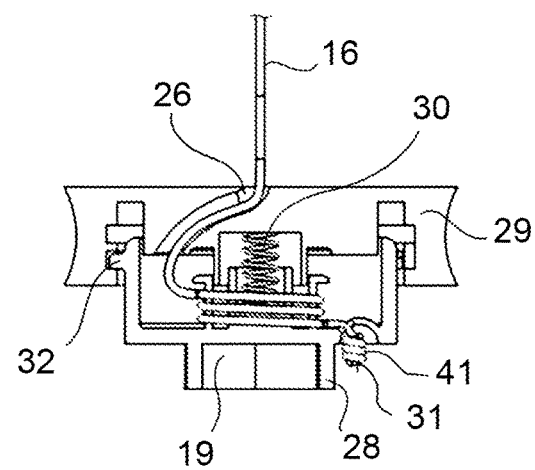
Figure 10A:
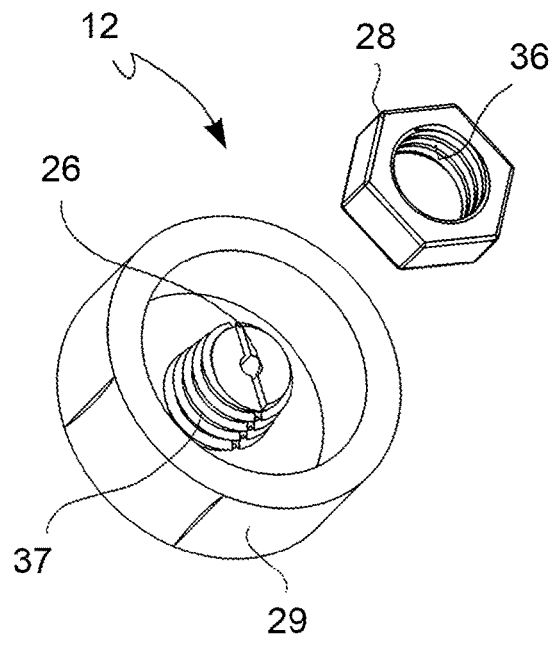
Figure 10B:
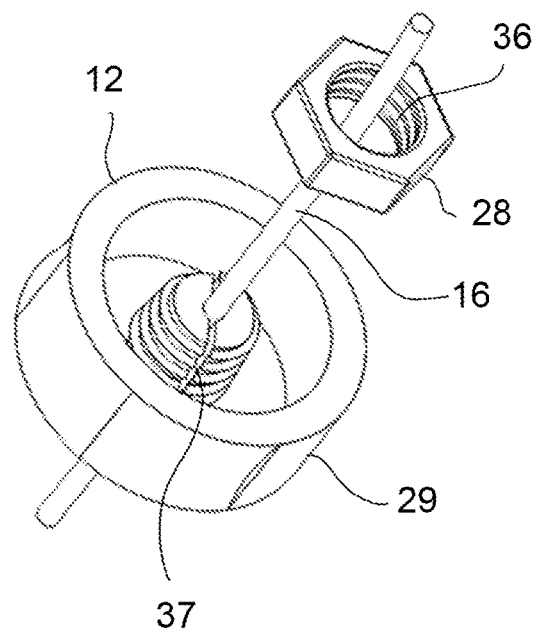
Figure 11:
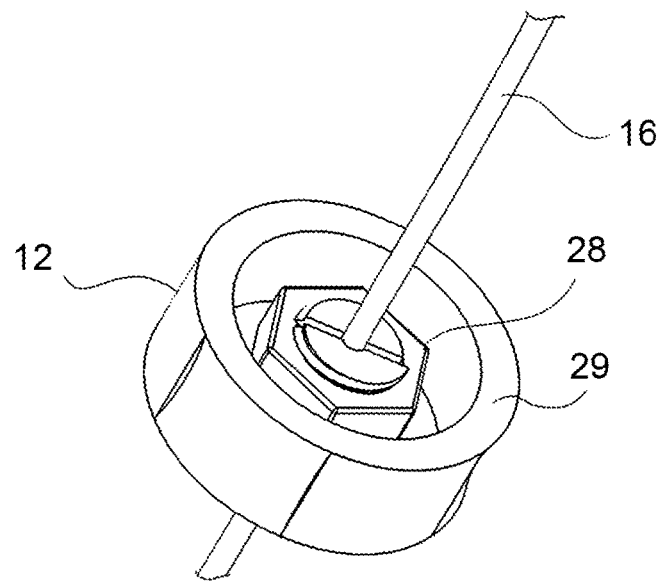
Figure 12A:
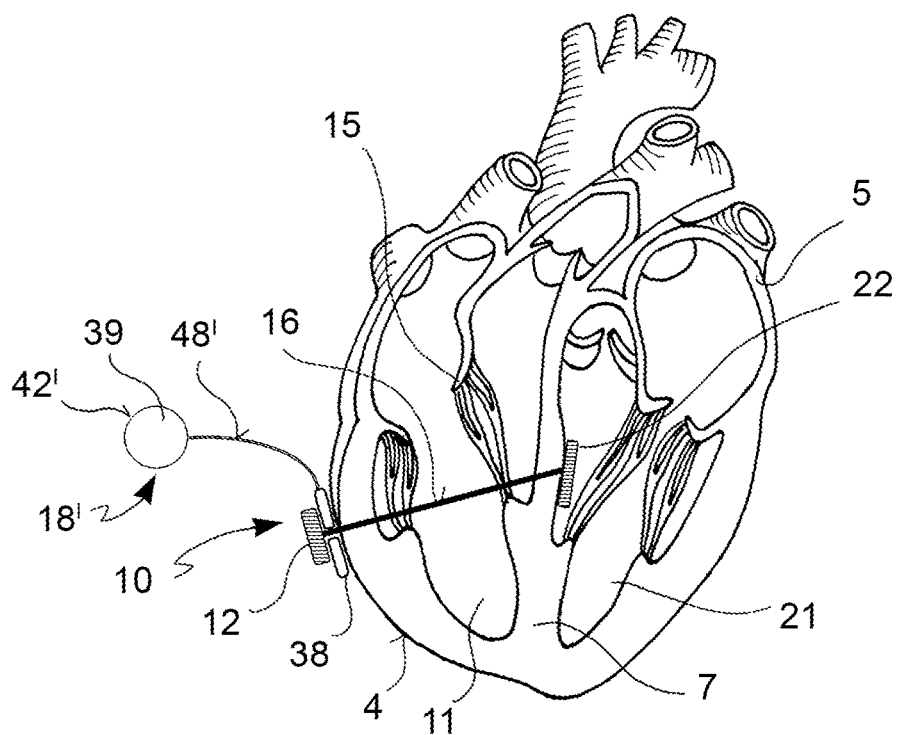
Figure 12B:
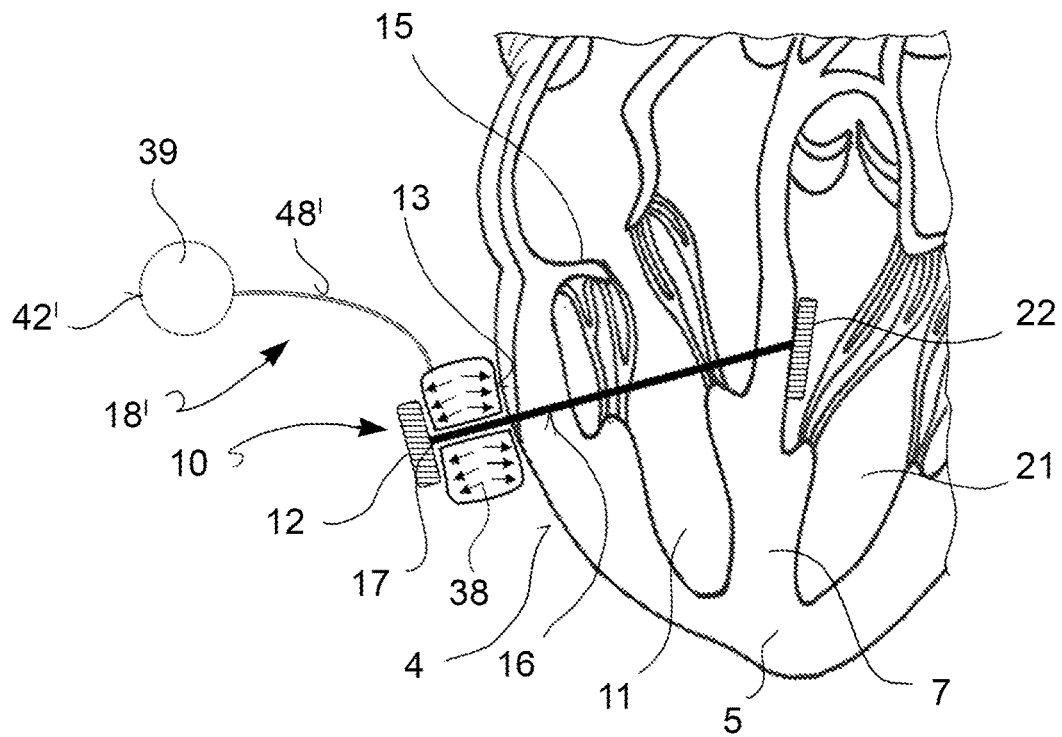
Figure 13A:
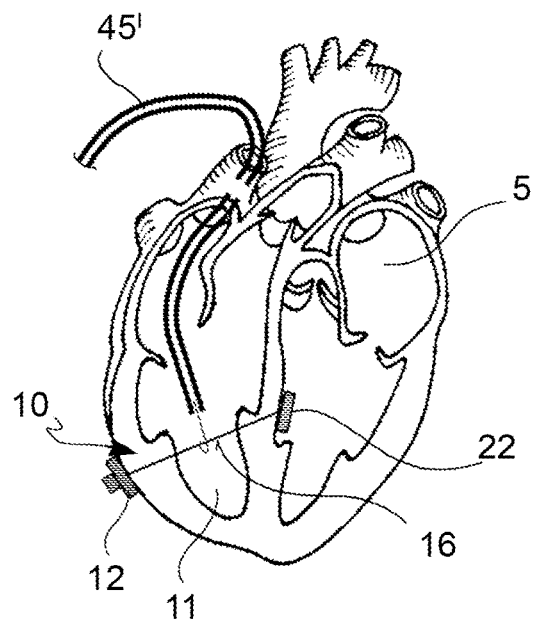
Figure 13B:
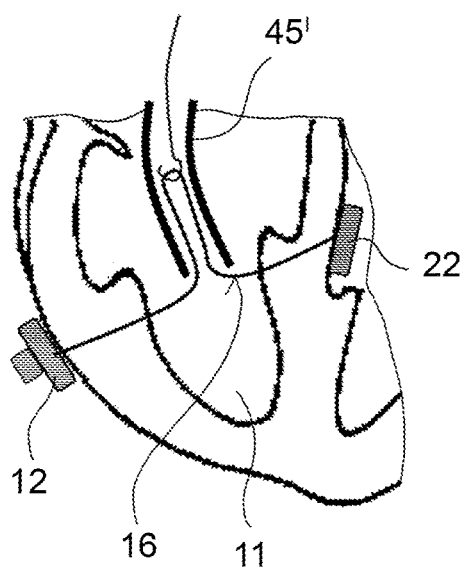
Figure 13C:
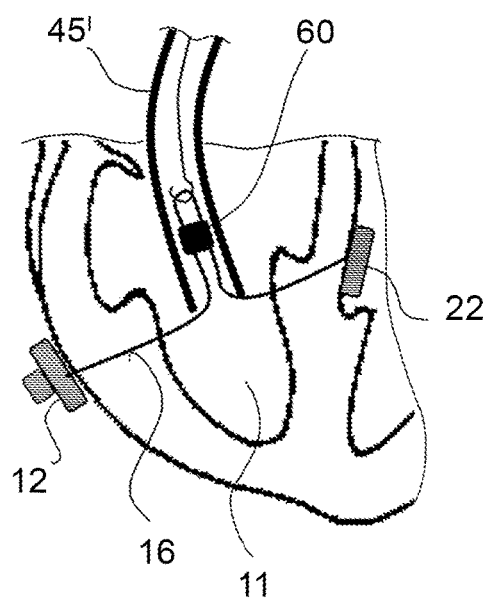
Figure 13D:
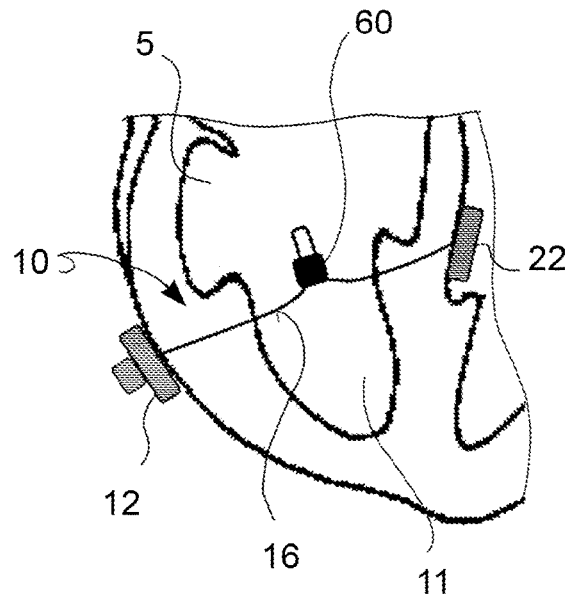
Figure 14:
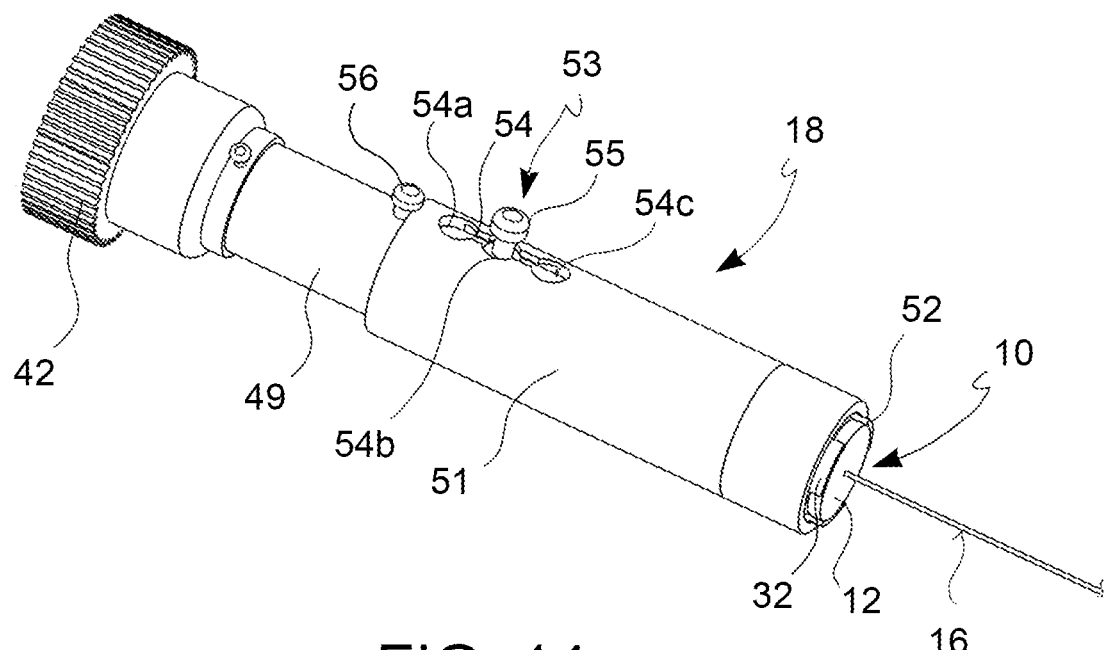
Figure 15:
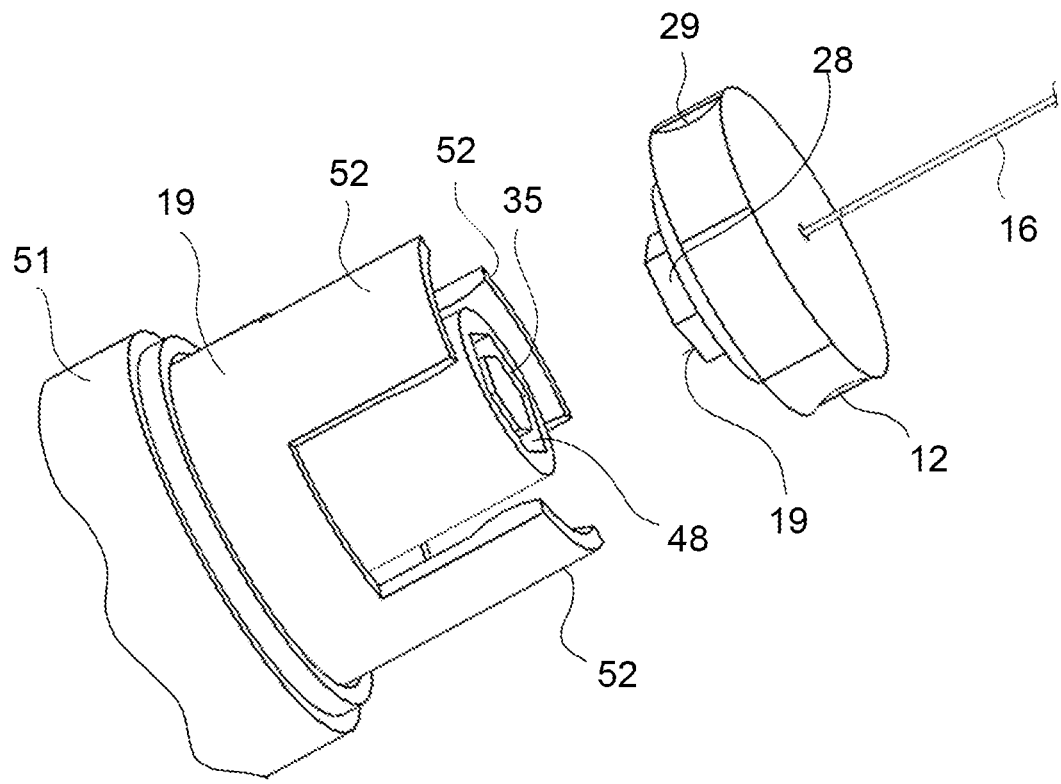
Figure 16:
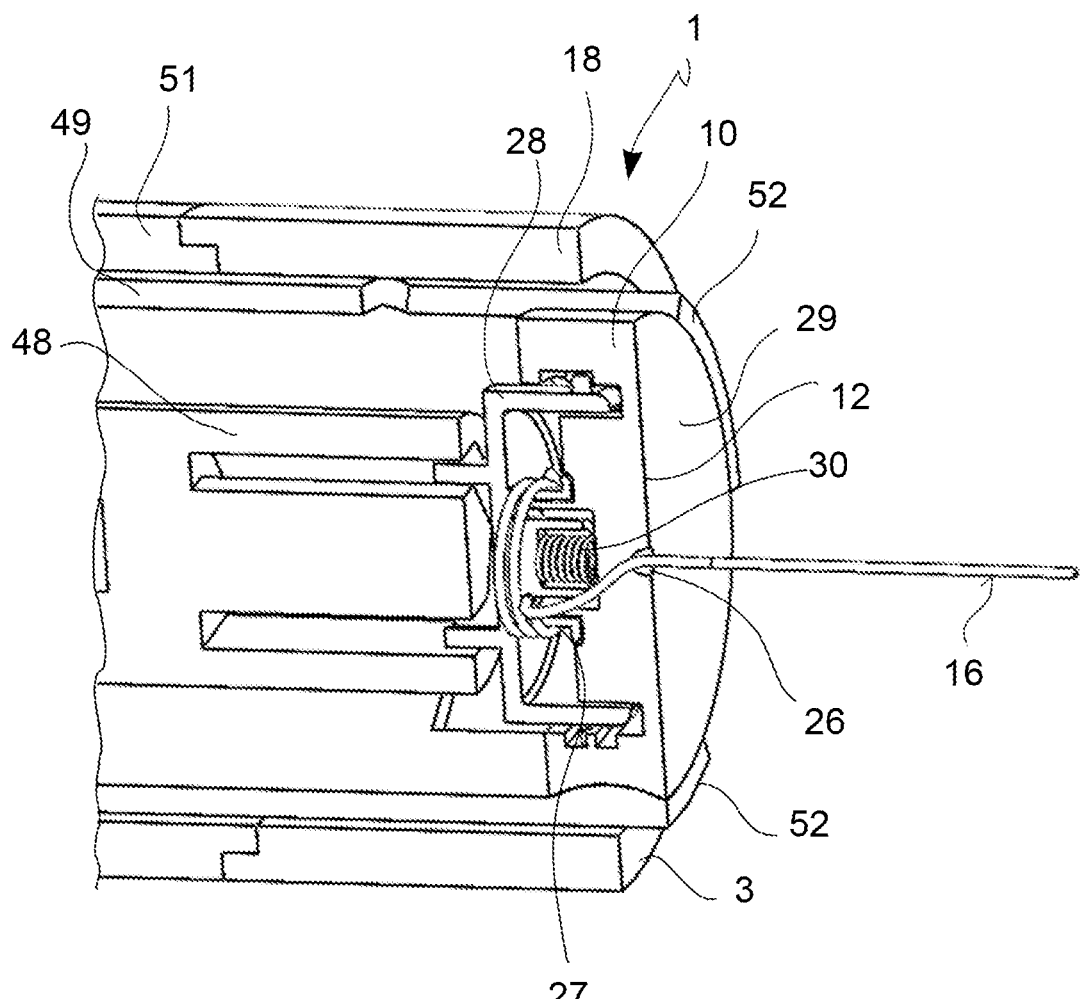
Figure 17:
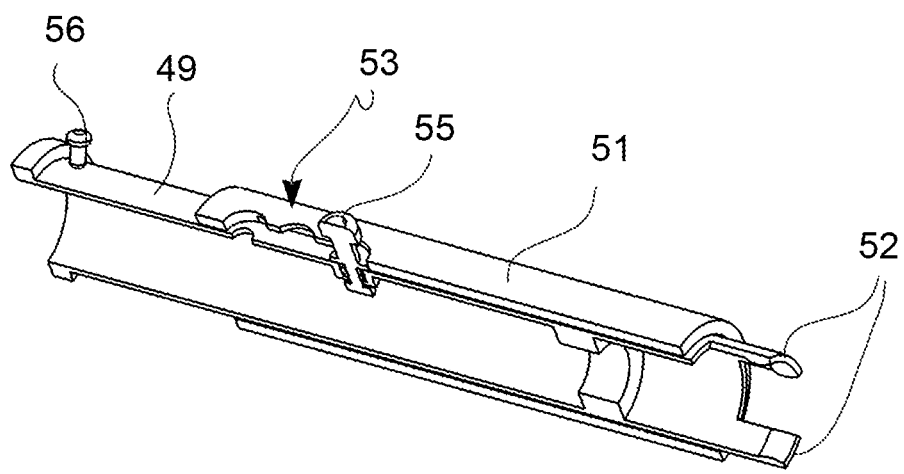
Figure 20B:
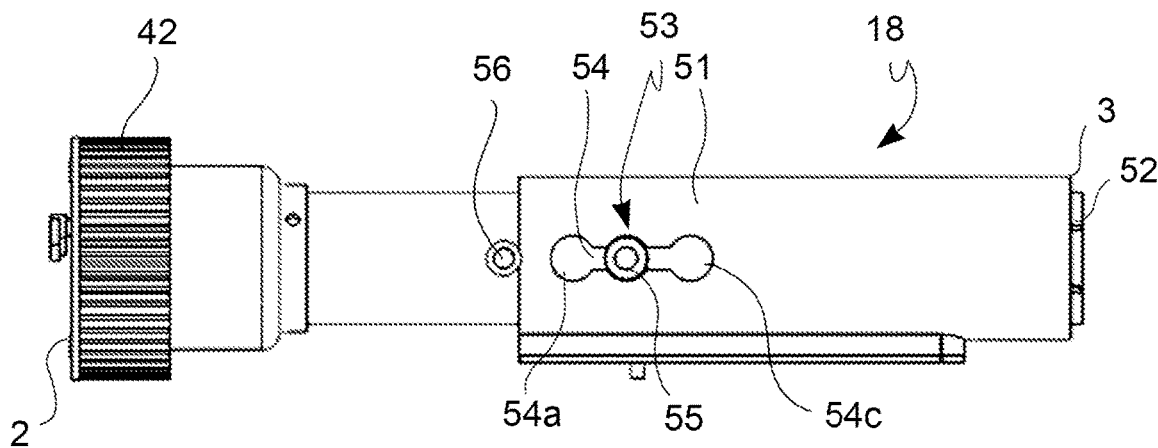
Figure 21A:
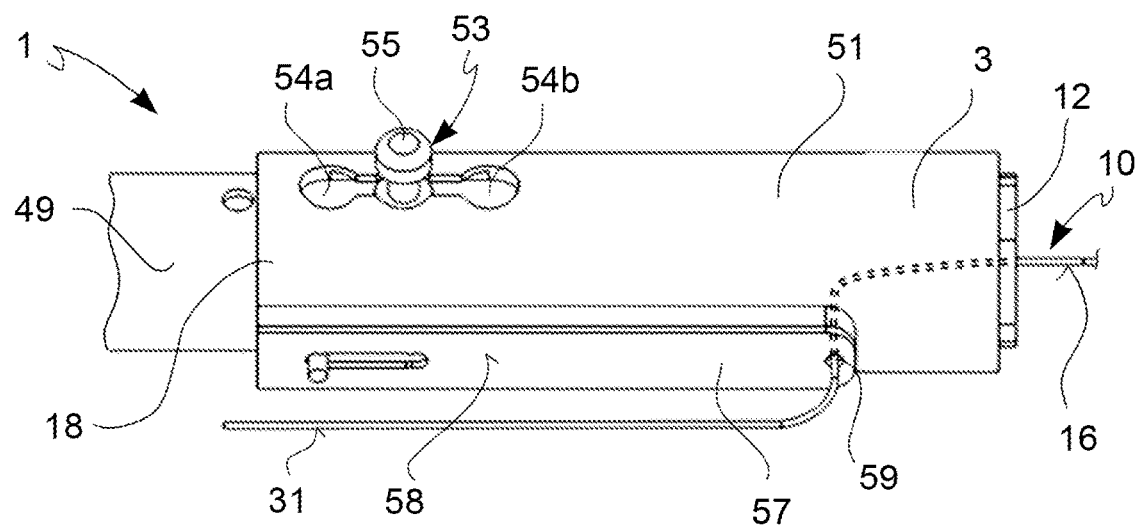
Figure 21B:
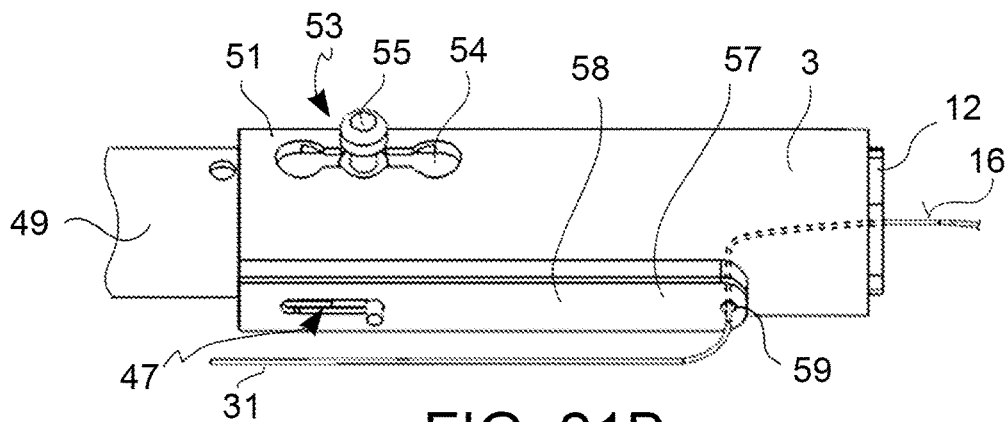
Figure 21C:
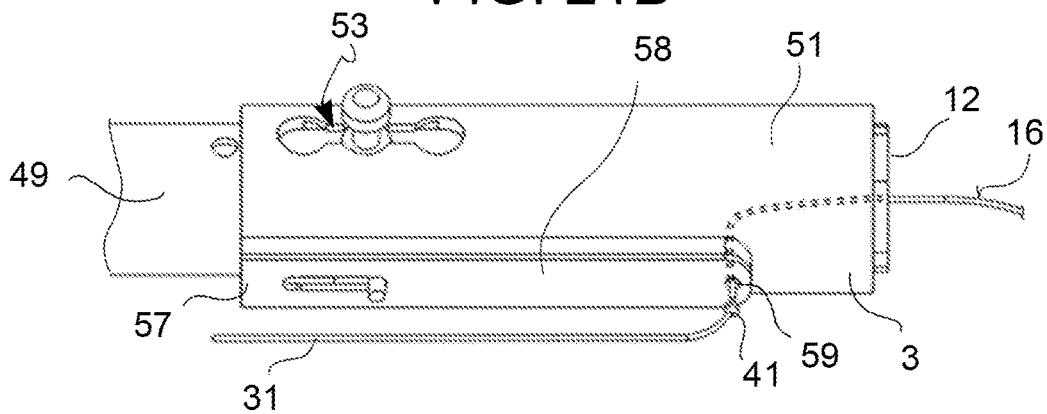
Figure 21D:
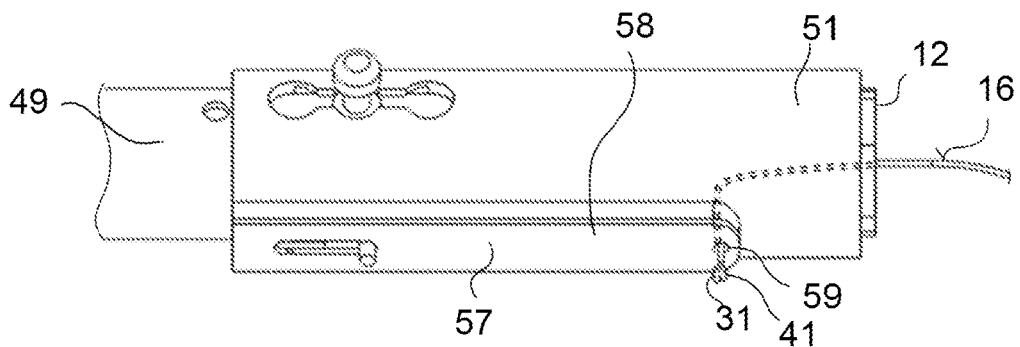
Figure 21E:
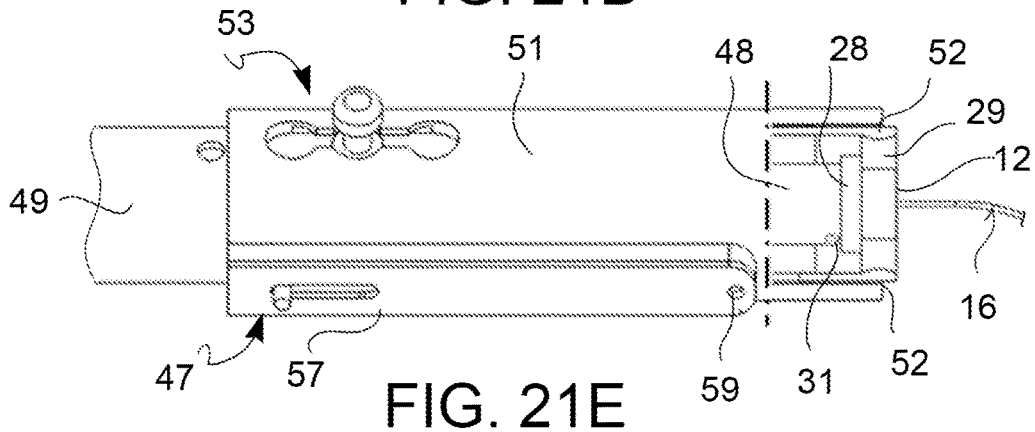

FIGS. 5A and 5 B diagrammatically show some steps of the implantation of the implantable device, according to a possible operating method;

FIG. 6 diagrammatically shows a possible step of the implantation of the implantable device, according to a possible operating method;

FIGS. 7A, 7 B and 7 C diagrammatically show some steps of the implantation of the implantable device subsequent to the steps shown in FIGS. 5-A and 5-B or in FIG. 6, according to a possible operating method;

FIG. 8 is an isometric view with separated parts of an anchoring element of an implantable device, according to an embodiment;

FIGS. 9A-9 F diagrammatically and sectionally show an adjustment sequence which is achievable by the anchoring element in FIG. 8;

FIG. 10A shows an axonometric view with separated parts of an anchoring element, according to an embodiment;

FIG. 10 B shows an axonometric view of the anchoring element in FIG. 10A during a possible adjustment sequence;

FIG. 11 shows an axonometric view and with assembled parts of the anchoring element in FIG. 10A locked on the tether;

FIGS. 12A and 12 B diagrammatically show an adjustment sequence, according to an embodiment;

FIGS. 13A, 13 B, 13 C and 13 D diagrammatically show an adjustment sequence, according to an embodiment;

FIG. 14 shows an axonometric view of an assembly, according to an embodiment;

FIG. 15 shows an axonometric view and with separated parts of a portion of an assembly, according to an embodiment;

FIG. 16 shows an axonometric and sectional view of a portion of an assembly, according to an embodiment;

FIG. 17 shows an axonometric and sectional view of a portion of an assembly, according to an embodiment;

FIG. 18 shows an axonometric view of a portion of an assembly, according to an embodiment;

FIG. 19 shows an axonometric and sectional view of a portion of an assembly, according to an embodiment;

FIGS. 20A, B and C show some configurations of an adjustment device in vertical elevation;

FIGS. 21A-21 E show some steps of an adjustment sequence.

DETAILED DESCRIPTION

In accordance with a general embodiment, an implantable device 10 is included for reshaping a ventricle 11, 21 in a patient. The implantable device 10 comprises at least one tether 16 and an active anchor 12 or first anchor 12. Preferably, the implantable device 10 is designed to reshape the right ventricle 11 of a patient's heart 5 for the treatment of the tricuspid valve 15.

The active anchor 12 comprises an abutment portion 13 adapted to abut against a structure of the ventricle 11, 21. Preferably, the terminology "ventricle structure" means a wall of the heart which delimits or is located inside the ventricle, such as an outer wall 4 of the patient's heart 5 delimiting the ventricular chamber or a papillary muscle 6 or an interventricular septum 7 of the heart 5. For example, the structure of the ventricle 11 is an outer wall 4 of the patient's heart 5 delimiting the ventricular chamber 11 so that the abutment portion 13 of the active anchor 12 of the implantable device 10 is adapted to abut against the outer wall 4 of the heart 5.

In accordance with an embodiment, when in the conditions of implantable device 10 implanted in the patient's heart 5, the active anchor 12 forms a crossing gate of the outer wall 4 of the heart 5, the abutment portion 13 of the active anchor 12 is outside the right ventricle 11 and abuts against the outer wall 4 of the heart 5, the tether 16 crosses the right ventricle 11 to connect to a second structure of the right ventricle 11, for example a wall of the interventricular septum 7 or a wall of a papillary muscle 6 of the right ventricle 11.

Those skilled in the art will appreciate that the implantable device 10 can also be implanted in a left ventricle 21 to reshape the left ventricle 21 for the treatment of the mitral valve.

In accordance with a preferred embodiment, the implantable device 10 comprises a second further anchor 22, opposite to the active anchor 12 with respect to the body of the tether 16. Preferably, the tether 16 is fixed to said second further anchor 22. In accordance with an embodiment, the second anchor 22 also comprises a second abutment portion 23 adapted to abut against a second structure of the ventricle 11, opposite to the first structure of the ventricle 11 where the active anchor 12 abuts, so that the active anchor 12 and the second anchor 22 have respective abutment portions 13, 23 opposite to each other and so that the tether 16 can exert a traction action between the two anchors 12, 22, consequently causing the reshaping of the ventricle 11, 21. In accordance with an embodiment, the second anchor 22 comprises a portion, for example a hook, for coupling to a second ventricle structure. For example, the abutment portion 23 of the second anchor 22 is intended to abut against a wall facing the left ventricle 21 of the interventricular septum 7 so that the second anchor 22 is in the left ventricle 21, the first anchor 12 is on the wall 4 of the heart 5 and the tether 16 extends from said first anchor 12 to said second anchor 22. In accordance with an embodiment, the second anchor 22 is different from the first anchor 12. The second further anchor 22 is preferably a passive anchor, and preferably does not comprise any device for adjusting the tensional state of the tether 16.

Advantageously, the active anchor 12 of the implantable device 10 comprises an adjustment device adapted to adjust the tensional state of the tether 16. The adjustment of the tensional state of the tether 16 is preferably obtained by varying the useful length of the tether 16, i.e., the working length of the tether 16 between the two anchors 12, 22. Adjusting the tensional state of the tether 16 can lead to a change in the useful length of the tether. Adjusting the tensional state of the tether 16 allows to adjust the traction force between the two anchors 12, 22. Adjusting the tensional state of the tether 16 allows to adjust the relative position of the two anchors 12, 22.

The tether 16 can comprise an elastic element, to provide an elastic influence action aimed at bringing the two anchors 12, 22 closer together or aimed at distancing the two anchors 12, 22 away from each other.

The tether 16 can comprise at least one section made of shape-memory material.

At least one anchor 12 or 22 of said two anchors 12, 22 can comprise at least one portion made of shape-memory material.

In accordance with a general embodiment, an assembly 1 is included for reshaping a ventricle in a patient comprising at least one implantable device 10 according to any of the previously described embodiments.

The assembly 1 further comprises a tool 18, which is non-implantable and detachably connectable to said implantable device 10. The tool 18 comprises a proximal portion 2 and a distal portion 3 opposite to said proximal portion 2. A longitudinal axis is defined between said proximal portion 2 and said distal portion 3 of the tool 18.

The active anchor 12 of the implantable device 10 is adapted to detachably connect to the distal portion 3 of the tool 18.

Advantageously, the distal portion 3 of the tool 18 comprises an adjustment key 48 adapted to cooperate with the adjustment device of the active anchor 12. By operating the adjustment key 48, it is possible to adjust the tensional state of the tether 16 by means of the operation of the adjustment device. The adjustment key 48 can have a distal head 35 with polygonal geometry adapted to engage a proximal portion of the active anchor 12 to perform the adjustment of the tensional state of the tether 16.

With further advantage, the proximal portion 2 of the tool 18 comprises a maneuvering interface 42 which is operatively connectable to said adjustment key 48 for adjusting the tensional state of the tether by acting on the maneuvering interface of the proximal portion 2 of the tool 18. Preferably, the maneuvering interface 42 is intended to remain outside the patient's body during the adjustment of the tensional state of the tether 16 while the distal portion 3 of the tool 18 is connected to the active anchor 12 inside the patient's body. The active anchor 12 can be placed on the outer wall 4 of the heart 5, preventing the tool 18 from having to penetrate inside the patient's heart 5 to adjust the tensional state of the tether 16.

In accordance with a preferred embodiment, the tool 18 also acts as a delivery tool at least for the active anchor 12 of the implantable device 10. In other words, the same tool 18 has the dual function of delivering the active anchor 12 in the implantation site and allowing the adjustment of the tensional state of the tether 16 of the implantable device 10 by activating the adjustment device of the active anchor 12 from outside the heart 5. As shown for example in FIG. 7-B, the active anchor 12 can be delivered on the outer wall 4 of the heart 5 by the tool 18, for example mounted on the distal end 3 of the tool 18.

In accordance with an embodiment, the tool 18 also acts as a delivery tool for the tether 16.

The inclusion of such a tool 18 allows to adjust the tensional state of the tether 16 both during the implantation of the implantable device 10 and, if necessary, in a step subsequent to the implantation, while avoiding having to access inside the patient's heart 5.

In accordance with an embodiment, the assembly 1 further comprises a delivery catheter 46 for delivering at least one portion of the implantable device 10. As shown for example in FIGS. 5-A and 5-B, the delivery catheter 46 is intended to deliver the second further anchor 22 to the respective implantation site, for example the wall facing the right ventricle 21 of the atrial septum 7, crossing the interventricular septum 7.

In accordance with an embodiment, the assembly 1 further comprises a vascular catheter for delivering at least one portion of the implantable device 10. As shown for example in FIG. 6, the vascular catheter 45 is intended to deliver the second further anchor 22 to the respective implantation site, for example the wall facing the right ventricle 21 of the atrial septum 7 crossing the patient's vascular system.

As shown for example in FIG. 7-A, after the second anchor 22 has been delivered to the respective implantation site, the tether 16 can be extended through the ventricle 11.

As shown for example in FIGS. 7-B and 7-C, the active anchor 12 is then delivered by means of the tool 18 and the tensional state of the tether 16 can be adjusted before the detachment of the active anchor 12 from the tool 18.

The tensional state of the tether 16 can be adjusted in various manners.

In accordance with a preferred embodiment, the adjustment device of the active anchor 12 of the implantable device 10 comprises two portions 28, 29 rotatably associated with each other. Thereby, by relatively rotating said two portions 28, 29 of the active anchor 12 with each other, it is possible to adjust the tensional state of the tether 16.

In accordance with a preferred embodiment, the tool 18 further comprises a shaft 49 fitted onto said adjustment key 48, so that the adjustment key 48 and the shaft 49 are rotatably associated with each other. Preferably, the adjustment key 48 of the tool 18 is integrally connectable to a first portion 28 of the adjustment device of the active anchor 12, and the shaft 49 of the tool 18 is integrally connectable to a second portion 29 of the adjustment device of the active anchor 12. Thereby, it is possible to adjust the tension of the tether by means of rotation impressed on the adjustment key 48, and preferably on the maneuvering interface 42.

The inclusion of such a tool 18 allows to adjust the tensional state of the tether 16 by rotating the maneuvering interface 42 both during the implantation of the implantable device 10 and, if necessary, in a step subsequent to the implantation, while avoiding having to access inside the patient's heart 5.

According to an embodiment, one portion 28 or 29 of said two portions 28, 29 of the adjustment device of the active anchor 12 is integrally connectable to the tether 16. Thereby, for example, it is possible to wind the tether 16 around a winding shaft 27 which can be included inside the active anchor 12. In accordance with an embodiment shown for example in FIGS. 9-A to 9-F, a proximal section 31 of the tether 16 has an enlarged portion, for example a knot 41, which acts as an end-of-stroke for integrally connecting the tether 16 to a first portion 28 of the adjustment device of the active anchor 12, so that a relative rotation of the two portions 28, 29 of the adjustment device causes the winding of a proximal portion of the tether 16 around a winding shaft 27. By virtue of the inclusion of such a winding shaft 27 it is possible to obtain a winch system for adjusting the tensional state of the tether. The winding shaft 27 can be provided in a single piece or integral with the first portion 28. The first portion 28 preferably comprises a termination site 17, for example a through hole of a comparable gauge to that of the tether 16, which is integrally connectable to a portion of the tether 16. The second portion 29 can comprise a central channel 26 which receives the tether 16. Preferably, the central channel 26 of the second portion 29 and the termination site 17 of the first portion 28 are offset from each other, i.e., they are not in axis, to cause the winding of the tether 16 around the winding shaft 27.

As shown for example in FIGS. 9-A and 9-B, the tether 16 is secured to the termination portion 17 of the anchoring element 12 by forming a knot 41 in the proximal section 31 of the tether 16. As shown for example in FIGS. 9-C and 9-D, by opposing the action of the spring 30, the two portions 28, 29 of the anchoring element 12 are released so that they can rotate with respect to each other, causing the proximal portion 31 of the tether 16 to be wound, which consequently tensions the tether 16. As shown for example in FIGS. 9-E and 9-F, the action of the spring 30 interlocks the two portions 28, 29 of the anchoring element 12 with each other in a predefined mutual configuration. Preferably, the winch adjustment system comprises one or more radial teeth 32 extending from a first portion 28 to be received in an annular groove 33 of a second portion 29 of the anchoring element 12, when the action of the spring 30 is opposed. When the action of the spring 30 is not opposed, said one or more radial teeth 32 abut against a circumferential abutment 34 which prevents the portions 28, 29 from rotating with respect to each other.

As shown for example in FIG. 8, a preload spring 30 can be included between the two portions 28, 29 of the anchoring element 12. Preferably, the spring 30 mutually distances the two portions 28, 29 of the anchoring element 12, interlocking them in a mutual configuration. By opposing the action of the spring 30, it is possible to unlock the configuration and rotate one portion 28 or 29 of the two portions 28, 29 with respect to the other 29 or 28, causing the tether 16 to be wound around the winding shaft 27. The winch adjustment system formed by said two portions 28, 29 of the anchoring element 12 can comprise a ratchet mechanism adapted to allow the relative rotation of the two portions 28, 29 in a single rotation direction.

The maneuvering interface 42 can comprise a ratchet mechanism adapted to allow the rotation of the maneuvering key 48 with respect to the shaft 49 in a single rotation direction.

In accordance with an embodiment, said two portions 28, 29 are rotatably associated with each other by means of threaded coupling. As shown for example in FIGS. 10-A, 10-B and 11, a portion 29 comprises a passage channel 26 adapted to receive with clearance the tether 16 arranged on a male threaded element 37 so that the tether can slide with respect to the portion 29, and in which the other portion 28 comprises a tightening nut 36 which, when screwed onto the male threaded element 37, causes a narrowing of the gauge of the passage channel 26, stopping the sliding of the tether 16 with respect to the male threaded element 37 of the portion 29 by friction.

In accordance with a preferred embodiment, the active anchor 12 of the implantable device 10 comprises an anchor back 19 opposite to said abutment portion 13, in which the distal portion 3 of the tool 18 is detachably connectable to said anchor back 19. When in operating conditions, the anchor back 19 is adapted to remain outside the ventricle 11. Thereby, the active anchor 12 forms a sort of adjustment gate for the tensional state of the tether 16 having the anchor back 19 placed on the outer wall 4 of the heart 5 so that it can be reached by the access device 18 even after the implantation of the implantable device 10, to adjust the tensional state of the tether 16 post-implantation without requiring an access inside the heart 5.

In accordance with a preferred embodiment, the tool 18 further comprises an outer case 51 slidingly associated with said shaft 49 so that the distal portion 3 of the tool 18 can protrude at various distances distally from the outer case 51. When in operating conditions, once the outer case 51 of the access device 18 has been positioned so that the distal end thereof is near the outer wall 4 of the heart 5, it is possible to advance the shaft 49 and the adjustment key 48 in the distal direction so that they can engage the active anchor 12, to adjust the tensional state of the tether 16.

In accordance with a preferred embodiment, the tool 18 comprises said maneuvering key 48 rotatable inside said longitudinally hollow shaft 49 and adapted to engage a first portion 28 of the active anchor, the tool 18 comprising at the distal end of said shaft 49 one or more fingers 52 which extend distally like a crenellation in order to engage, for example in a snap-fit manner, the second portion 29 of the active anchor 12. Preferably, the set of the maneuvering key 48 and shaft 49 are capable of moving forward and backward with respect to the case 51. An advancement control 53 can be included in order to cause the relative moving forward and/or backward of the case 51 with respect to the set of the maneuvering key 48 and the shaft 49, formed for example by a longitudinal slot 54 placed on the case 51 which defines a plurality of seats 54-*a*, 54-*b*, 54-*c* adapted to receive a radial pin 55 extending the shaft 51 so as to lock the set of the maneuvering key 48 and shaft 49 in a mutual position with respect to the case of the access device 18. Said seats 54-*a*, 54-*b*, 54-*c* are preferably aligned in the longitudinal direction of the tool 18. An end-of-stroke pin 56 can be included which is integral with the shaft 49, forming a proximal abutment for the case 51.

The inclusion of such a pin 55 and such a slot 54 allows to mechanically visualize the relative position in which the set of the maneuvering key 48 and shaft 49 with respect to the case 51 is located.

Figure 20C:
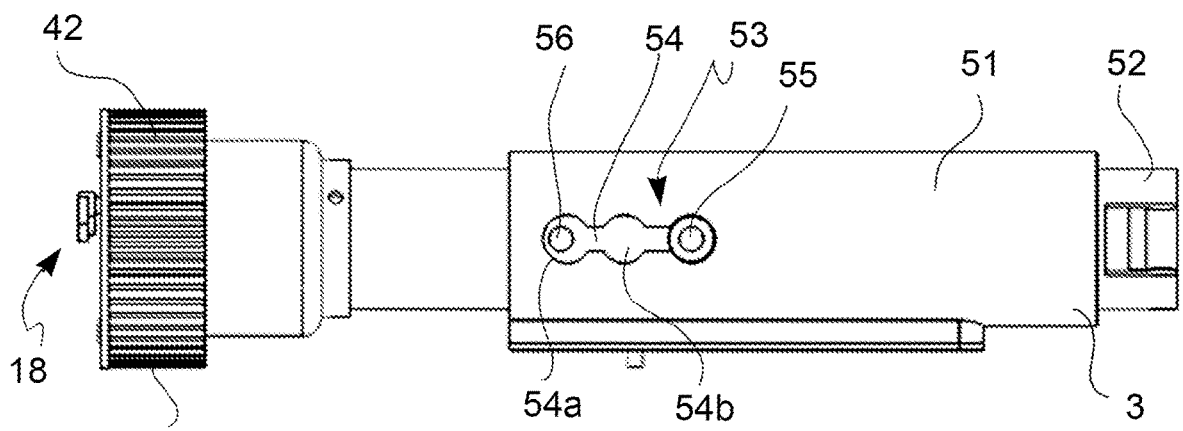

As shown for example in FIGS. 20-B and 20-C, by distally advancing the maneuvering key 48 and the shaft 49 with respect to the case 51, the pin 55 is moved from the seat 54-*b* to the seat 54-*c*.

In accordance with an embodiment, the tool 18 comprises a tether guiding device 57 adapted to guide a proximal portion 31 of the tether 16. For example, the tether guiding device 57 comprises a perforated plate 58 arranged on the case 51, in which the hole 59 of the perforated plate 58 of the tether guiding device 57 receives a proximal portion of the tether 16. By virtue of the inclusion of said tether guiding device 57, it is possible to temporarily lock a proximal section 31 of tether 16 having a predetermined length in order to obtain said knot 41 or said enlarged portion 41 on the proximal section 31 of the tether 16. Furthermore, by virtue of the inclusion of said tether guiding device 57 it is possible to preassemble the active anchor 12 to the distal end 3 of the tool 18, in other words, by virtue of the inclusion of said tether guiding device 57, it is possible to provide an assembly 1 having the active anchor 12 of the implantable device 10 preassembled on the tool 18, avoiding assembling the active anchor 12 on the tool 18 during the operation. For example, as shown in FIG. 21-A, the proximal portion 31 of the tether 16 passes through the active anchor 12, the tool 18 in a proximal direction and exits from the hole 59. As shown in FIG. 21-B, by activating the command 47, the diameter of the hole 59 is reduced, locking the proximal portion 31 of the tether 16 in the hole 59 by friction. As shown in FIGS. 21-C and 21-D a knot 41 or an enlarged portion is made on the proximal portion 31 of the tether 16 and the section of the tether 16 proximal to the knot 41 is cut. As shown in FIG. 21-E, the command 47 is deactivated and the section of the hole 59 passes through the tether 16 and the knot 41, so that by distally advancing the knot 41 it abuts the termination portion 17 of the active anchor 12. The inclusion of such a tether guiding device 57 also allows the tether 16 to be kept close to the case 51.

In accordance with an embodiment, the adjustment device of the active anchor 12 of the implantable device 10 comprises an expandable element 38, for example an inflatable balloon. By expanding the expandable balloon 38, the termination portion 17 to which the tether 16 is secured is distanced from the abutment portion 13 of the active anchor 12. The abutment portion 13 of the active anchor 12 can be included on the expandable element 38. The expandable element 38 is integrally connectable to the termination portion 17 in a portion thereof. In this case, in order to adjust the tensional state of the tether 16 it is necessary to inflate the expandable element 38, and the inflation of the expandable element 38 can be achieved by using a percutaneous port 18' having a fluid communication duct with the expandable element 38, to expand it, in which the fluid communication duct 48' therefore acts as an adjustment key 48', the percutaneous port 18' being provided with an inflation tank 39 having a maneuvering interface 42', for example a deformable pouch when pressed. By applying pressure to the deformable pouch, which acts as a maneuvering interface 42', the inflation fluid moves from the inflation tank 39 to the expandable element 38 which thereby distancing the tether termination portion 17 from the abutment portion 13 of the active anchor 12 allows to tension the tether 16.

In accordance with a preferred embodiment, the active anchor 12 comprises two portions 28, 29 slidingly coupled so that a relative distancing of the two portions allows to adjust the tensional state of the tether 16, acting as an adjustment device. In accordance with a preferred embodiment, the two mutually slidingly coupled portions of the anchoring element 12 can be interlocked with each other, acting as a locking device. The sliding coupling between the two portions 28, 29 can be included in addition to or in place of the rotatable coupling between the two portions 28, 29.

According to an embodiment, as shown for example in the FIGS. 13-A to 13-D, the adjustment of the tensional state of the tether 16 can occur by means of a cardiac catheter 45' with vascular access which delivers a forceps 60, for example an elastic clip 60, inside the ventricle 11 in order to adjust the tensional state of the tether 16. Thereby the adjustment of the tensional state of the tether 16 can occur either by acting on the active anchor 12 by means of the tool 18 or by means of a trans-catheter action performed with a cardiac catheter 45'. Preferably, the cardiac catheter 45' comprises at the distal end thereof an elastic clip 60, preferably detachably connected to the cardiac catheter 45, so as to deliver it inside the ventricle 11 in order to adjust the tensional state of the tether 16.

The adjustment of the tensional state of the tether 16 carried out by means of a trans-catheter approach can be included in place of the adjustment of the tensional state of the tether 16 obtained by means of the active anchor 12.

According to a general embodiment, an assembly 1 for reshaping a ventricle in a patient comprises an implantable device 10 for reshaping a ventricle comprising a tether 16, and a cardiac catheter 45' for adjusting the tensional state of the tether 16. The cardiac catheter 45' is preferably a vascular access catheter adapted to reach the ventricle 11, 21, for example the right ventricle 11, of the patient's heart 5 with a distal portion thereof. The cardiac catheter 45' preferably comprises at the distal end thereof forceps 60 or a clip 60 for adjusting the tensional state of the tether 16 of the implantable device 10, as shown for example in FIGS. 13-A to 13-D. The implantable device preferably comprises two opposite anchors at opposite ends of the tether 16. For example, the implantable device 10 is adapted to reshape a ventricle to repair a heart valve, for example to repair the tricuspid valve 15.

By virtue of the features described above provided separately or jointly with each other in particular embodiments, it is possible to obtain a device as well as an assembly which at the same time satisfies the above described requirements, contrasting each other, and the aforementioned desired advantages, and in particular:

- it allows to adjust the tensional state of the tether of an implantable device for reshaping a ventricle, in order to repair a heart valve;
- the adjustment can occur with a trans-thoracic tool;
- it allows to adjust the tension of the tether by maneuvering a maneuvering interface placed outside the patient's body, at the proximal end of the trans-thoracic tool;
- the trans-thoracic tool can also act as a device for delivering the active anchor of the implantable device;
- it allows to adjust the tensional state of the tether after implantation, without requiring direct access to the ventricle;
- the active anchor forms an adjustment gate for the tether placed on the outer wall of the heart;
- the active anchor acts as a device for adjusting the tensional state of the tether;
- it allows to repair a heart valve by approximating, i.e., by bringing closer together, the structures of the ventricle such as the ventricular walls, the interventricular septum, the papillary muscles, a combination of the above.

Those skilled in the art may make many changes and adaptations to the embodiments described above or may replace elements with others, which are functionally equivalent, in order to meet contingent needs without however departing from the scope of the appended claims.

LIST OF REFERENCE NUMERALS

1 Assembly
2 Proximal portion of the tool
3 Distal portion of the tool
4 Outer wall of the heart
5 Heart
6 Papillary muscle
7 Interventricular septum
10 Implantable device
11 Right ventricle
12 Active anchor or first anchor
13 Abutment portion
15 Tricuspid valve
16 Tether
17 Termination portion
18, 18' Tool
19 Anchor back
21 Left ventricle
22 Second anchor
23 Second abutment portion
26 Channel
27 Winding shaft
28 First portion of the active anchor
29 Second portion of the active anchor
30 Spring
31 Proximal section of the tether
32 Radial teeth
33 Annular groove
34 Circumferential abutment
35 Distal head of the adjustment key
36 Nut
37 Male threaded element
38 Expandable element
39 Inflation tank
41 Knot, or enlarged portion, of the tether
42, 42' Adjustment key maneuvering interface
45' Vascular catheter
46 Delivery catheter
48, 48' Adjustment key
49 Tool shaft
51 Tool case
52 Distal fingers of the shaft
53 Advancement command
54 Slot
54 a-c Seats
55 Radial pin
56 End-of-stroke
57 Tether guiding device
58 Perforated plate
59 Hole
60 Forceps or clip

We claim:

1. A method of treating regurgitation in a patient's heart having a ventricle, an intraventricular septum and an atrioventricular valve, the method comprising:
providing an implantable assembly including an active anchor, a septal anchor and a tether having a working portion extending between the active anchor and the septal anchor and a proximal portion associated with the active anchor;
positioning the septal anchor adjacent the intraventricular septum;
locating the active anchor adjacent a wall of the ventricle, the active anchor including an abutment portion adapted to abut against the wall and a tether portion rotatably coupled to the abutment portion; and
engaging the tether portion of the active anchor with an adjustment tool and applying a rotational force to the tether portion such that a relative rotation of the portions adjusts a first length of the working portion and a second length of the proximal portion of the tether;
wherein decreasing the first length of the working portion increases a tension of the working portion of the tether so as to reshape the ventricle; and
wherein the locating step includes coupling the active anchor to a distal end of the adjustment tool and positioning the abutment portion of the active anchor adjacent the wall of the ventricle using a proximal portion of the adjustment tool.

2. The method of claim 1 wherein the positioning step includes advancing a catheter through the intraventricular septum and using the catheter to dispose the septal anchor adjacent the septum.

3. The method of claim 1 wherein the locating step includes coupling the active anchor to a distal end of a delivery tool and positioning the abutment portion of the active anchor adjacent the wall of the ventricle using a proximal portion of the delivery tool.

4. The method of claim 3 further including coupling a hollow shaft of the adjustment tool to the abutment portion of the active anchor and coupling an adjustment component of the adjustment tool to the tether portion of the active anchor and wherein rotation of the adjustment component causes the relative rotation of the portions of the active anchor.

5. The method of claim 1 further comprising coupling the proximal portion of the tether to the tether portion of the active anchor.

6. The method of claim 5 wherein the coupling step includes forming an enlarged portion in the proximal portion of the tether.

7. The method of claim 6 wherein the enlarged portion is a knot and further wherein a portion of the tether proximal to the knot is removed.

8. The method of claim 1 wherein a proximal portion of the adjustment tool includes a maneuvering interface adapted to allow a user to impart relative rotation to the adjustment component.

9. The method of claim 1 wherein a distal end of the hollow shaft includes an engagement member configured to engage the abutment portion so as to resist rotation thereof.

10. The method of claim 9 wherein the engagement member includes a plurality of fingers extending from the distal end of the hollow shaft.

11. The method of claim 1 wherein the tether portion includes a winding shaft configured such that the relative rotation causes the proximal portion of the tether to wind around the winding shaft.

12. The method of claim 1 wherein the locating step includes coupling an end of the proximal portion of the tether to the tether portion of the active anchor.

13. The method of claim 1 wherein the abutment portion and the tether portion include a locked configuration and an adjustment configuration, the active anchor further comprising a biasing mechanism for biasing the active anchor in the locked configuration, the method further comprising applying a force to the tether portion sufficient to overcome the biasing mechanism and transition the active anchor into the adjustment configuration.

14. The method of claim 13 wherein in the adjustment configuration, the relative rotation of the portions of the active anchor can occur in both directions.

15. The method of claim 1 further comprising, post-implantation, engaging the tether portion of the active anchor with the adjustment component of the adjustment tool and further adjusting the length of the working portion.

16. A method of treating regurgitation in a patient's heart having a ventricle, an intraventricular septum and an atrio-ventricular valve, the method comprising:
   providing an implantable assembly including an active anchor, a septal anchor and a tether having a working portion extending between the active anchor and the septal anchor and a proximal portion associated with the active anchor;
   positioning the septal anchor adjacent the intraventricular septum;
   locating the active anchor adjacent a wall of the ventricle, the active anchor including an abutment portion adapted to abut against the wall and a tether portion rotatably coupled to the abutment portion; and
   engaging the tether portion of the active anchor with an adjustment tool and applying a rotational force to the tether portion such that a relative rotation of the portions adjusts a first length of the working portion and a second length of the tether proximal portion;
   wherein decreasing the first length of the working portion increases a tension of the working portion of the tether so as to reshape the ventricle; and
   wherein the engaging step includes coupling a hollow shaft of the adjustment tool to the abutment portion of the active anchor and coupling an adjustment component of the adjustment tool to the tether portion of the active anchor and wherein rotation of the adjustment component causes the relative rotation of the portions of the active anchor.

17. The method of claim 16 wherein the tether portion of the active anchor includes a connection site adapted to couple with the end of the proximal portion of the tether.

18. A method of treating regurgitation in a patient's heart having a ventricle, an intraventricular septum and an atrio-ventricular valve, the method comprising:
   providing an implantable assembly including an active anchor, a septal anchor and a tether having a working portion extending between the active anchor and the septal anchor and a proximal portion associated with the active anchor;
   coupling the active anchor to a distal end of a delivery tool;
   positioning the septal anchor adjacent the intraventricular septum;
   locating the active anchor adjacent a wall of the ventricle, the active anchor including an abutment portion adapted to abut against the wall and a tether portion rotatably coupled to the abutment portion; and
   positioning the abutment portion of the active anchor adjacent the wall of the ventricle using a proximal portion of the delivery tool:
   coupling a hollow shaft of the adjustment tool to the abutment portion of the active anchor and coupling an adjustment component of the adjustment tool to the tether portion of the active anchor; and
   applying a rotational force to the tether portion, by rotating the adjustment component, such that a relative rotation of the portions of the active anchor adjusts a first length of the working portion and a second length of the tether proximal portion;
   wherein decreasing the first length of the working portion increases a tension of the working portion of the tether so as to reshape the ventricle.

* * * * *